US012685307B2

(12) United States Patent
Jin et al.

(10) Patent No.: US 12,685,307 B2
(45) Date of Patent: Jul. 21, 2026

(54) ULTRA-HIGH DENSITY CELL BANKING METHODS

(71) Applicant: Genzyme Corporation, Cambridge, MA (US)

(72) Inventors: Xiaoxia Jin, Bridgewater, NJ (US); Claudia Buser, Bridgewater, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 18/113,281

(22) Filed: Feb. 23, 2023

(65) Prior Publication Data

US 2023/0309551 A1      Oct. 5, 2023

Related U.S. Application Data

(63) Continuation of application No. 14/857,766, filed on Sep. 17, 2015, now abandoned.

(60) Provisional application No. 62/052,257, filed on Sep. 18, 2014.

(51) Int. Cl.
| | |
|---|---|
| *A01N 1/125* | (2025.01) |
| *C12M 1/00* | (2006.01) |
| *C12M 3/06* | (2006.01) |
| *C12N 5/073* | (2010.01) |

(52) U.S. Cl.
CPC .......... *A01N 1/125* (2025.01); *C12N 5/0603* (2013.01); *C12M 23/14* (2013.01); *C12M 27/16* (2013.01); *C12M 29/10* (2013.01)

(58) Field of Classification Search
None
See application file for complete search history.

(56) References Cited

U.S. PATENT DOCUMENTS

| | | | |
|---|---|---|---|
| 6,100,061 A | 8/2000 | Reiter et al. | |
| 6,475,725 B1 | 11/2002 | Reiter et al. | |
| 6,544,424 B1 | 4/2003 | Shevitz | |
| 6,544,788 B2 | 4/2003 | Singh | |
| 8,084,252 B2 | 12/2011 | Reiter et al. | |
| 8,153,425 B2 | 4/2012 | Pogue-Caley et al. | |
| 2003/0054331 A1 | 3/2003 | Fraser et al. | |
| 2005/0173315 A1 | 8/2005 | Bosch et al. | |
| 2006/0166364 A1 | 7/2006 | Senesac | |
| 2010/0098725 A1 | 4/2010 | Liu et al. | |

| | | | | |
|---|---|---|---|---|
| 2012/0329151 A1* | 12/2012 | Baskar | .................. | C12M 41/26 |
| | | | | 435/351 |
| 2014/0011270 A1 | 1/2014 | Chotteau et al. | | |
| 2014/0273206 A1 | 9/2014 | Jin et al. | | |

FOREIGN PATENT DOCUMENTS

| | | | | |
|---|---|---|---|---|
| EA | 200900188 A1 | 6/2009 | | |
| EP | 2308958 A2 * | 4/2011 | ............ | C07K 16/00 |
| EP | 3193594 A1 | 7/2017 | | |
| RU | 2290808 C2 | 1/2007 | | |
| RU | 2314687 C1 | 1/2008 | | |
| RU | 2012111734 A | 9/2013 | | |
| WO | 1996/026266 A1 | 8/1996 | | |
| WO | 1997/005240 A1 | 2/1997 | | |
| WO | 2000/011102 A1 | 3/2000 | | |
| WO | 2001/038362 A2 | 5/2001 | | |
| WO | 2005/095578 A1 | 10/2005 | | |
| WO | 2008/006494 A1 | 1/2008 | | |
| WO | 2011/091248 A1 | 7/2011 | | |
| WO | 2011/140241 A2 | 11/2011 | | |
| WO | 2012/128703 A1 | 9/2012 | | |
| WO | 2013/006461 A1 | 1/2013 | | |
| WO | 2014/143691 A1 | 9/2014 | | |
| WO | 2016/044670 A1 | 3/2016 | | |

OTHER PUBLICATIONS

Clincke, M.-F. et al. May 2013. Very high density of CHO cells in perfusion by ATF or TFF in WAVE BioreactorTM—Part II: Applications of antibody production and cryopreservation. American Institute of Chemical Engineers 29(3): 768-777; specif. pp. 768, 769, 770, 775 (Year: 2013).*
Seth, G. et al. Jan. 2013. Development of a new bioprocess scheme using frozen seed train intermediates to initiate CHO cell culture manufacturing campaigns. Biotechnology and Bioengineering 110(5): 1376-1385; specif. pp. 1376, 1377, 1378, 1380, 1381 (Year: 2013).*
GE Healthcare. First published 2003. WAVE bioreactor systems: cell culture procedures. pp. 1-52; specif. pp. 13, 14, 17 (Year: 2003).*
Clincke, M.-F. et al. Part I. May 2013. Very high density of CHO cells in perfusion by ATF or TFF in WAVE Bioreactor. Part I. Effect of the cell density on the process. Biotechnology Progress 29(3): 754-767; specif. pp. 754, 755 (Year: 2013).*
Seth, G. 2012. Freezing mammalian cells for production of biopharmaceuticals. Review article. Methods 56: 424-431; specif. p. 427 (Year: 2012).*

(Continued)

*Primary Examiner* — Blaine Lankford
(74) *Attorney, Agent, or Firm* — MH2 Technology Law Group, LLP

(57) ABSTRACT

Provided are methods for the creation of ultra-high density cryopreserved cell banks. In certain embodiments, these methods employ altered perfusion culture techniques that allow for production of ultra-high density cell cultures that can be cryopreserved at unexpectedly high cell densities without the need for any cell concentration steps, while retaining excellent cell viability and quality.

21 Claims, 24 Drawing Sheets

(56) References Cited

OTHER PUBLICATIONS

Bitter et al., "Expression and Secretion Vectors for Yeast," Methods Enzymol., 1987, vol. 153, pp. 516-544.

Clincke et al., "Very High Density of CHO Cells in Perfusion by ATF or TFF in WAVE Bioreactor™. Part I. Effect of the Cell Density on the Process," Biotechnology Progress, May 2013, vol. 29, No. 3, pp. 754-767.

Clincke et al., "Very High Density of Chinese Hamster Ovary Cells in Perfusion by Alternating Tangential Flow or Tangential Flow Filtration in WAVE Bioreactor™—Part II: Applications for Antibody Production and Cryopreservation," Biotechnology Progress, May 2013, vol. 29, No. 3, pp. 768-777.

Logan et al., "Adenovirus Tripartite Leader Sequence Enhances Translation of mRNAs Late After Infection," Proc. Nall. Acad. Sci. USA., 1984, vol. 81, pp. 3655-3659.

Nieminen et al., "The Use of the ATF System to Culture Chinese Hamster Ovary Cells in a Concentrated Fedbatch System," BioPharm International, 2011, vol. 24, Issue 6, pp. 1-8.

Ninomiya et al., "Large-Scale, High-Density Freezing of Hybridomas and Its Application to High-Density Culture," Biotechnol. Bioeng., 1991, vol. 38, pp. 1110-1113.

Ozturk, "Engineering Challenges in High Density Cell Culture Systems," Cytotechnology, 1996, vol. 22, pp. 3-16.

Seth et al., "Development of a New Bioprocess Scheme Using Frozen Seed Train Intermediates to Initiate CHO Cell Culture Manufacturing Campaigns," Biolechnol. Bioeng. 2013, vol. 110, No. 5, pp. 1376-1385.

Singh, "Disposable Bioreactor for Cell Culture Using Wave-Induced Agitation," Cytotechnology, 1999, vol. 30, pp. 149-158.

Spectrum Laboratories, Inc. "Hollow Fiber Filters," Datasheet [online]. Accessible on the Internet at URL: http://www.spectrumlabs.com/filtration/mPESKrosFloList.html. [Last Accessed on Jun. 12, 2015].

Tao et al., "Development and Implementation of a Perfusion-Based High Cell Density Cell Banking Process," Biotechnology Progress, Apr. 2011, vol. 27, No. 3, pp. 824-829.

Woods et al., "Container System for Enabling Commercial Production of Cryopreserved Cell Therapy Products," Regenerative Medicine, 2010, vol. 5, No. 4, pp. 659-667.

International Search Report with Written Opinion issued in International Patent Application No. PCT/US2014/027757, mailed Aug. 20, 2014.

International Search Report with Written Opinion issued in International Patent Application No. PCT/US2015/050817, mailed Nov. 27, 2015.

Heidemann et al., "Characterization of Cell-Banking Parameters for the Cryopreservation of Mammalian Cell Lines in 100-ml Cryobags," Biotechnology Progress, 2010, vol. 26, No. 4, pp. 1154-1163.

Chotteau et al., "Study of Alternating Tangential Flow Filtration for Perfusion and Harvest in Chinese Hamster Ovary Cells Cultivation," In; The Proceedings of the Cell Culture Engineering Conference XII, Apr. 25-30, 2010, Banff, Canada, Accessible on the Internet at URL: http://kth.diva-portal.org/smash/record.jsf?pid=diva2%3A501600&dswid=7668. [Last Accessed Aug. 17, 2017].

GE Healthcare, WAVE Bioreactor Systems, Cell Culture Procedures, Procedure 28-9308-65 AA, Copyright 2003-2008 General Electric Company, Aug. 2008, First Published 2003, pp. 1-52.

Yuk et al., "Overcoming Challenges in WAVE Bioreactors Without Feedback Controls for pH and Dissolved Oxygen," Biotechnology Progress, 2011, vol. 27, No. 5, pp. 1397-1406.

Eibl et al., "Bag Bioreactor Based Wave-Induced Motion: Characteristics and Applications," Advanced Biochemical, Engineering/Biotechnology, 2009, vol. 115, pp. 55-87.

Pall Life Sciences (L. Schwartz, Senior Technical Manager, and K. Seeley, Ph.D., Scientific and Laboratory Services), "Introduction to Tangential Flow Filtration for Laboratory and Process Development Applications," Scientific & Technical Report, PN 33213, Feb. 2003, 12 pages.

* cited by examiner

ULTRA-HIGH DENSITY CELL BANKING METHODS

RELATED APPLICATIONS

This application is a continuation of U.S. patent application Ser. No. 14/857,766, filed Sep. 17, 2015, which claims priority to U.S. Provisional Patent Application Ser. No. 62/052,257, filed Sep. 18, 2014, the entire disclosures of which are hereby incorporated herein by reference.

BACKGROUND

Cell banking is widely used to maintain stocks of frozen, characterized cells that may be thawed for use in a number of applications, including the production of therapeutically relevant proteins. Typically, cryopreserved stocks are maintained at lower densities (e.g., about 1 or $2 \times 10^7$ cells/mL) or are centrifuged to create higher density aliquots for storage. Lower density stocks do not allow for efficient inoculation of large volume cultures, and concentration methods can damage cells, thereby reducing cell viability of the frozen stock. For these reasons, previous methods of cell banking are relatively inefficient, and ultimately do not allow for rapid production of high density cell cultures from frozen stocks. Accordingly, there is a need for improved cell banking methods.

SUMMARY

The current disclosure provides improved methods for the creation of an ultra-high density cell bank. In certain embodiments, the methods of the invention employ improved perfusion cell culture techniques that allow for production of ultra-high density cell cultures that can be cryopreserved at unexpectedly high cell densities without the need for any cell concentration steps, while retaining excellent cell viability for later use in production cell culture.

Accordingly, in one aspect, the instant disclosure provides a method for producing an ultra-high density frozen cell bank directly from a population of cultured cells, the method comprising: culturing cells in a perfusion bioreactor to obtain an ultra-high density cell population with a concentration of at least $1.0 \times 10^8$ cells/mL, wherein said perfusion bioreactor is coupled to a cell retention system; and adding cryoprotectant to the ultra-high density cell population to produce an ultra-high density frozen cell bank, wherein the ultra-high density frozen cell bank has a concentration of at least $1.0 \times 10^8$ cells/mL, and wherein no additional concentrating step is performed between culturing the cells and adding cryoprotectant to the ultra-high density cell population.

In certain embodiments, the cell retention system comprises an alternating tangential flow filtration system comprising a filter. In certain embodiments, the filter has a surface area of at least about 0.08 m². In certain embodiments, the filter has a surface area of about 0.08 m² to about 0.3 m², about 0.3 m² to about 0.5 m², about 0.5 m² to about 1.0 m², about 0.7 m² to about 0.8 m², about 1.0 m² to about 2.0 m², about 2.0 m² to about 3.0 m², about 3.0 m² to about 4.0 m², or about 4.0 m² to about 5.5 m². In certain embodiments, the filter has a pore size selected from the group consisting of 0.2 μm, 0.4 μm, and 0.65 μm. In other embodiments, the filter has a pore size selected from the group consisting of 0.7 μm, 1.2 μm, and 7 μm.

In certain embodiments, the ultra-high density cell population has a viable cell density selected from the group consisting of about $1.0 \times 10^8$ cells/mL, about $1.1 \times 10^8$ cells/mL, about $1.2 \times 10^8$ cells/mL, about $1.3 \times 10^8$ cells/mL, about $1.4 \times 10^8$ cells/mL, about $1.5 \times 10^8$ cells/mL, about $1.6 \times 10^8$ cells/mL, about $1.7 \times 10^8$ cells/mL, about $1.8 \times 10^8$ cells/mL, about $1.9 \times 10^8$ cells/mL, and about $2.0 \times 10^8$ cells/mL.

In certain embodiments, cryopreserving comprises adding dimethyl sulphoxide (DMSO) to the ultra-high density cell population at a final concentration of about 5% to about 10%, vol/vol. In certain embodiments, cryopreserving comprises freezing at least a portion of the ultra-high density cell population in a container appropriate for storage under cryopreservation conditions.

In certain embodiments, the container is a vial. In certain embodiments, the ultra-high density frozen cell bank comprises about $4.5 \times 10^8$ cells/vial.

In certain embodiments, the container is a cryobag. In certain embodiments, the cryobag has a volume of about 5 to about 150 mL. In certain embodiments, the ultra-high density frozen cell bank has a cell density of at least about $1.0 \times 10^8$ cells/mL.

In certain embodiments, the perfusion rate in the perfusion bioreactor is between about 0.02 nL/cell/day to about 0.5 nL/cell/day. In certain embodiments, the perfusion rate in the perfusion bioreactor is between 0 and 15 reactor volumes per day.

In certain embodiments, the perfusion bioreactor cell culture has a pH of between about 6.8 to about 7.2.

In certain embodiments, the perfusion bioreactor cell culture has a dissolved oxygen concentration (DO) of at least about 30%.

In certain embodiments, the bioreactor is a flexible bag bioreactor. In certain embodiments, the bioreactor comprises a built-in filter.

In certain embodiments, the ultra-high density frozen cell bank has a post-thaw cell viability of at least about 60%, at least about 70%, at least about 80%, at least about 90%, or at least about 95%.

In certain embodiments, the cells are mammalian cells. In certain embodiments, the mammalian cells are selected from the group consisting of: CHO, CHO-DBX11, CHO-DG44, CHO-S, CHO-K1, Vero, BHK, HeLa, COS, MDCK, HEK-293, NIH-3T3, W138, BT483, Hs578T, HTB2, BT20, T47D, NS0, CRL7030, HsS78Bst cells, PER.C6, SP2/0-Ag14, and hybridoma cells. In certain embodiments, the cells are transfected cells. In certain embodiments, the cells express a therapeutic protein.

In certain embodiments: the perfusion bioreactor comprises a flexible bag bioreactor; the filter has a filter surface area of at least 0.3 m² and a molecular weight cut off (MWCO) size of at least 50 kDa; the cryoprotectant added to the ultra-high density cell population is DMSO; and the ultra-high density frozen cell bank comprises about 5% to about 10%, vol/vol DMSO.

In certain embodiments, the pH and DO of the culture are controlled by automated methods. In certain embodiments, the pH and DO of the culture are controlled by non-automated methods. In certain embodiments, the pH and DO are controlled through any one or more of the following: adjustment of the mixture of gases that are introduced to the culture, adjustment of the rock rate of the bioreactor, or adjustment of the rock angle of the bioreactor. In certain embodiments, the bioreactor is rocked at 15 rpm with a rock angle of 8°. In certain embodiments, the bioreactor is rocked at 22 rpm with a rock angle of 10°. In certain embodiments, the bioreactor is rocked at 25 rpm with a rock angle of 12°.

In certain embodiments, the ultra-high density cell population is cooled to and maintained at a temperature of about 4° C. prior to and during the addition of the cryoprotectant and dispensing. In certain embodiments, the ultra-high density cell population is maintained at a temperature of about 20° C. to about 26° C. during the addition of the cryoprotectant and dispensing. In certain embodiments, the ultra-high density cell population is maintained at an uncontrolled cold temperature by using an ice-water bath during the addition of the cryoprotectant and dispensing.

DETAILED DESCRIPTION

Figure 1:
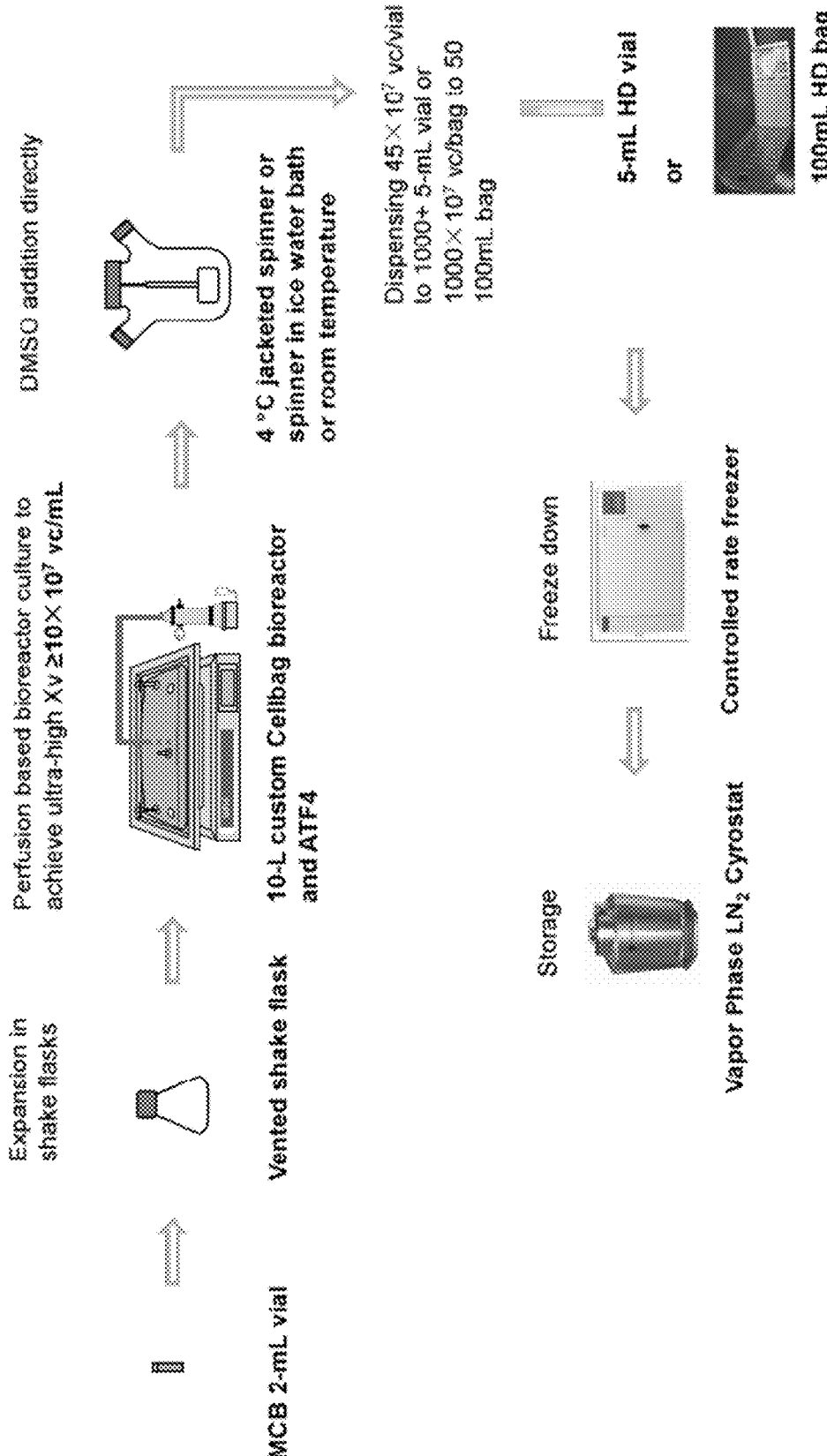
FIG. 1: is a drawing of an ultra-high density cell cryobanking process.

The current disclosure provides a method of ultra-high density cell cryobanking that comprises the use of a perfusion culture system linked to a non-centrifugal cell retention device.

I. Definitions

As used herein, the term "batch culture" refers to a cell culturing technique in which a quantity of fresh culture medium is inoculated with cells that rapidly enter a logarithmic growth phase and in which the growth medium of the culture is not continuously removed and replaced with fresh medium.

As used herein, the term "fed batch culture" refers to a cell culturing technique in which a quantity of fresh culture medium is inoculated with cells initially, and additional culture nutrients are fed (continuously or in discrete increments) to the culture during the culturing process, with or without periodic cell and/or product harvest before termination of culture.

As used herein, the term "perfusion culture" refers to a cell culturing technique in which a quantity of fresh medium is inoculated with cells that rapidly enter a logarithmic growth phase (as above) and in which the growth medium is continuously removed from a culture and replaced with fresh medium.

As used herein, the term "bioreactor" shall refer to a vessel for culturing cells.

In one embodiment, the bioreactor is a "flexible bag bioreactor". A "flexible bag bioreactor" is a sterile chamber capable of receiving a liquid media and cell inoculum which additionally comprises connectors, ports, adaptors and flexible tubing. In one embodiment, the chamber is made of plastic. In a specific embodiment, the chamber is made of multilayered laminated clear plastic. In a further specific embodiment, the chamber is made of multilayer laminated clear plastic and has a fluid contact layer made of USP Class VI ethylene vinyl acetate/low density polyethylene copolymer while the outer layer is made of low density polyethylene.

Additionally, the connectors, ports, and adaptors may be made from any kind of plastic including but not limited to: polyethylene, polypropylene, and polycarbonate while the tubing may be constructed from any kind of plastic including but not limited to: thermoplastic elastomer or silicone (e.g. platinum-cured silicone).

Appropriate flexible bag bioreactors can be commonly found in the art and include, but are not limited to, those described in U.S. Pat. No. 6,544,788, which is herebyincorporated by reference in its entirety.

The flexible bag bioreactor can be partially filled with culture media and then inflated to rigidity. It may then be placed on a rocking platform (such as a BASE20/50EHT rocking unit from GE Life Sciences) that moves back and forth through a preset rocking angle and preset rocking rate. This rocking motion induces wave-like motions in the culture media, promoting agitation and oxygen transfer in order to improve the performance of the cell culture. The preset rocking angle may be at least about 4 degrees, e.g. about 4 degrees, 5 degrees, 6 degrees, 7 degrees, 8 degrees, 9 degrees, 10 degrees, 11 degrees, or 12 degrees. Furthermore, the preset rocking rate may be set at rock rate per minute (rpm) that is at least about 6 rpm, e.g. about 6 rpm, about 7 rpm, 8 rpm, 9 rpm, 10 rpm, 11 rpm, 12 rpm, 13 rpm, 14 rpm, 15 rpm, 16 rpm, 17 rpm, 18 rpm, 19 rpm, 20 rpm, 21 rpm, 22 rpm, 23 rpm, 24 rpm, 25 rpm, 26 rpm, 27 rpm, 28 rpm, 29 rpm, 30 rpm, 31 rpm, 32 rpm, 33 rpm, 34 rpm, 35 rpm, 36 rpm, 37 rpm, 38 rpm, 39 rpm, or 40 rpm. In a specific embodiment, the rock rate per minute is about 22 rpm.

As used herein, the term "cell retention system" refers to all devices with the ability to separate cells from medium and the waste products therein by the use of a filter. Filters may include membrane, ceramic, or metal filters in any shape including spiral wound, tubular, or sheet. Filters may be of different surface areas. For example, the filter surface area may be about $0.08$ m$^2$ to about $5.5$ m$^2$, e.g. about $0.08$ m$^2$, $0.09$ m$^2$, $0.1$ m$^2$, $0.2$ m$^2$, $0.3$ m$^2$, $0.4$ m$^2$, $0.5$ m$^2$, $0.6$ m$^2$, $0.7$ m$^2$, $0.77$ m$^2$, $0.8$ m$^2$, $0.9$ m$^2$, $1.0$ m$^2$, $1.1$ m$^2$, $1.2$ m$^2$, $1.3$ m$^2$, $1.4$ m$^2$, $1.5$ m$^2$, $1.6$ m$^2$, $1.7$ m$^2$, $1.8$ m$^2$, $1.9$ m$^2$, $2.0$ m$^2$, $2.1$ m$^2$, $2.2$ m$^2$, $2.3$ m$^2$, $2.4$ m$^2$, $2.5$ m$^2$, $2.6$ m$^2$, $2.7$ m$^2$, $2.8$ m$^2$, $2.9$ m$^2$, $3.0$ m$^2$, $3.1$ m$^2$, $3.2$ m$^2$, $3.3$ m$^2$, $3.4$ m$^2$, $3.5$ m$^2$, $3.6$ m$^2$, $3.7$ m$^2$, $3.8$ m$^2$, $3.9$ m$^2$, $4.0$ m$^2$, $4.1$ m$^2$, $4.2$ m$^2$, $4.3$ m$^2$, $4.4$ m$^2$, $4.5$ m$^2$, $4.6$ m$^2$, $4.7$ m$^2$, $4.8$ m$^2$, $4.9$ m$^2$, $5.0$ m$^2$, $5.1$ m$^2$, $5.2$ m$^2$, $5.3$ m$^2$, $5.4$ m$^2$, or $5.5$ m$^2$. In certain embodiments, the filter module has a molecular weight cut off (MWCO) size from about 10 kilodaltons (kDa) to about 100 kDa, e.g. it is about 10 kDa, 20 kDa, 30 kDa, 40 kDa, 50 kDa, 60 kDa, 70 kDa, 80 kDa, 90 kDa, or 100 kDa. In other embodiments, the filter module has a mesh size from about 0.1 μm to about 7 μm, e.g. about 0.1 μm, 0.2 μm, 0.3 μm, 0.4 μm, 0.5 μm, 0.6 μm, 0.7 μm, 0.8 μm, 0.9 μm, 1.0 μm, 1.1 μm, 1.2 μm, 1.3 μm, 1.4 μm, 1.5 μm, 1.6 μm, 1.7 μm, 1.8 μm, 1.9 μm, 2.0 μm, 2.1 μm, 2.2 μm, 2.3 μm, 2.4 μm, 2.5 μm, 2.6 μm, 2.7 μm, 2.8 μm, 2.9 μm, 3.0 μm, 3.1 μm, 3.2 μm, 3.3 μm, 3.4 μm, 3.5 μm, 3.6 μm, 3.7 μm, 3.8 μm, 3.9 μm, 4.0 μm, 4.1 μm, 4.2 μm, 4.3 μm, 4.4 μm, 4.5 μm, 4.6 μm, 4.7 μm, 4.8 μm, 4.9 μm, 5.0 μm, 5.1 μm, 5.2 μm, 5.3 μm, 5.4 μm, 5.5 μm, 5.6 μm, 5.7 μm, 5.8 μm, 5.9 μm, 6.0 μm, 6.1 μm, 6.2 μm, 6.3 μm, 6.4 μm, 6.5 μm, 6.6 μm, 6.7 μm, 6.8 μm, 6.9 μm, or 7.0 μm.

As used herein, the term "cryopreservation" refers to a process by which cells, tissues, or any other substances susceptible to damage caused by time or by enzymatic or chemical activity are preserved by cooling and storing them to sub-zero temperatures.

As used herein, the term "cryobanking" refers to a technique by which cells are mixed with a cryoprotectant (e.g., DMSO with or without hydroxyethyl starch (HES)) and placed in a container appropriate for storage under cryopreservation conditions. These containers are then frozen using techniques well known in the art and stored at low temperatures, typically between about −130° C. and about −196° C. The collection of cells obtained by the process is a cell bank.

In one embodiment, the cell bank is an ultra-high density cell bank. As used herein, the term "ultra-high density cell bank" shall refer to cryobanked aliquots of cells that have been frozen at an ultra-high density, wherein the density is at least about $1{\times}10\hat{\ }8$ viable cells/mL, e.g. about $1{\times}10\hat{\ }8$ viable cells/mL, about $1.1{\times}10\hat{\ }8$ viable cells/mL, about $1.2{\times}10\hat{\ }8$ viable cells/mL, about $1.3{\times}10\hat{\ }8$ viable cells/mL, about $1.4{\times}10\hat{\ }8$ viable cells/mL, about $1.5{\times}10\hat{\ }8$ viable cells/ mL, about $1.6{\times}10\hat{\ }8$ viable cells/mL, about $1.7{\times}10\hat{\ }8$ viable cells/mL, about $1.8{\times}10\hat{\ }8$ viable cells/mL, about $1.9{\times}10\hat{\ }8$ viable cells/mL, about $2{\times}10\hat{\ }8$ viable cells/mL, about $3{\times}10\hat{\ }8$ viable cells/mL, about $4{\times}10\hat{\ }8$ viable cells/mL, or about $5{\times}10\hat{\ }8$ viable cells/mL. The cells may be frozen according to any method available in the art and in any container appropriate for storage under cryopreservation conditions.

In another embodiment, the cell bank is a master cell bank. As used herein, the term "master cell bank" shall refer to a culture of cells (e.g., fully characterized cells) that has been grown from a single clone, dispensed into storage containers (e.g., dispensed into the containers in a single operation), and stored under cryopreservation conditions as described above. In certain embodiments, the cells are suitable for later use in a production cell culture and a further harvest of the therapeutically relevant proteins produced thereby.

In another embodiment, the cell bank is a working cell bank. As used herein, the term "working cell bank" shall refer to a culture of cells (e.g. fully characterized cells) that has been grown from a single vial of the master cell bank, or from two pooled vials of the master cell bank, dispensed into storage containers (e.g., dispensed into the containers in a single operation), and stored under cryopreservation conditions as described above. In certain embodiments, the cells are suitable for later use in a production cell culture and a further harvest of the therapeutically relevant proteins produced thereby.

In another embodiment, the cell bank is a mini cell bank. As used herein, the term "mini-bank" shall refer to aliquots of cells that have been cryopreserved according to "cryobanking" procedures (as described above) but are composed of fewer samples than would normally be used to create a cell bank. This type of bank may be generally used to optimize the conditions being considered for the cryopreservation of a cell line before cell banks such as a "master cell bank" are created. As an example, a "mini-bank" is used to determine the optimal cell density for the ultra-high density cell banking procedure described in this disclosure.

As used herein, the term "container appropriate for storage under cryopreservation conditions" includes any container that may be used under conditions appropriate for cell storage between about −130° C. and about −196° C. These containers include, but are not limited to, vials that are made of materials suitable for cryopreservation. These materials include polymers (e.g., polytetrafluoroethylene, polystyrene, polyethylene, or polypropylene). Furthermore, surface treatments may be applied to a surface of the cryopreservation vial in order to improve cryopreservation conditions (e.g., hydrophilic coatings which reduce adsorption and denaturation). In exemplary embodiments, the vial may have a volume of more than about 0.1 mL, e.g. the vial may have a volume of about 0.1 mL, about 0.5 mL, about 0.75 mL, about 1 mL, about 1.5 mL, about 2 mL, about 2.5 mL, about 4.5 mL, about 10 mL, about 15 mL, about 20 mL, about 25 mL, or about 50 mL. The container may also be a cryobag, which may have a volume of about 30 mL, about 50 mL, about 100 mL, about 150 mL, about 200 mL, about 300 mL, about 400 mL, or about 500 mL.

As used herein, the term "cryobag" is a sterile chamber that is capable of receiving a liquid medium, is appropriate for cell storage between about −130° C. and about −196° C., and may additionally comprise connectors, ports, adaptors and flexible tubing. The cryobag may be constructed of any appropriate material including, but not limited to, polymers such as polytetrafluoroethylene (PTFE), polystyrene, polyethylene, polypropylene, Fluorinated Ethylene Propylene (FEP), polyolefin, and ethylene vinyl acetate (EVA). Exemplary cryobags include but are not limited to: KryoSure® Cryopreservation bags (Saint-Gobain), PermaLife™ Bags (OriGen Biomedical), CryoStore freezing bags (OriGen Biomedical), Freeze-Pak™ Biocontainers (Charter Medical), and bags disclosed in U.S. Provisional Application No. 62/037,181 (Merial Ltd., a Sanofi company), which is incorporated by reference herein in its entirety. In certain embodiments, the cryobag can support a closed phase cell banking system (e.g., through the use of at least two-sterile-weldable conduits allowing for "closed system" filling of the bags).

As used herein, the term "shake flask" shall refer to a vessel used as a culture flask in which the medium and cell culture is constantly agitated during incubation.

As used herein, the term "shake flask seed train" shall refer to a method of cell expansion in which an aliquot of cells is first cultured (seeded) in a shake flask and grown therein. The cells are cultured according to their growth rate and are usually split into larger and/or multiple vessels during their growth until the biomass reaches a level sufficient to inoculate a bioreactor.

As used herein, the term "seed density" shall refer to the initial cell density at which a flask or bioreactor is inoculated.

As used herein, the term "therapeutically relevant protein" shall refer to any protein that may be used to create a treatment for a disease or disorder or to treat a disease or disorder in an animal, including mammals such as mice, rats, monkeys, apes, and humans. These proteins may include, but are not limited to, binding polypeptides such as monoclonal antibodies, Fc fusion proteins, anticoagulants, blood factors, bone morphogenetic proteins, engineered protein scaffolds, enzymes, growth factors, hormones, interferons, interleukins, and thrombolytics.

As used herein, the term "binding polypeptide" or "binding polypeptide" shall refer to a polypeptide (e.g., an antibody) that contains at least one binding site which is responsible for selectively binding to a target antigen of interest (e.g., a human antigen). Exemplary binding sites include an antibody variable domain, a ligand binding site of a receptor, or a receptor binding site of a ligand. In certain aspects, binding polypeptides comprise multiple (e.g., two, three, four, or more) binding sites.

As used herein, the term "antibody" refers to such assemblies (e.g., intact antibody molecules, antibody fragments, or variants thereof) which have significant known specific immunoreactive activity to an antigen of interest (e.g., a tumor-associated antigen). Antibodies and immunoglobulins comprise light and heavy chains, with or without an interchain covalent linkage between them. Basic immunoglobulin structures in vertebrate systems are relatively well understood.

The generic term "antibody" comprises five distinct classes of antibody that can be distinguished biochemically. All five classes of antibodies are clearly within the scope of the current disclosure, the following discussion will generally be directed to the IgG class of immunoglobulin molecules. With regard to IgG, immunoglobulins comprise two identical light chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

As used herein, the term "dissolved oxygen" or "DO" is the percentage of dissolved oxygen gas present in a given liquid (such as cell culture medium) based on air saturation.

As used herein, the term "cell specific perfusion rate" (CSPR) shall refer to the rate in which the cell culture medium is fed to the cell culture expressed as the volume of medium added per viable cell per day (Ozturk, SS. Engineering challenges in high density culture systems. Cytotechnology. 1996; 22:3-16).

As used herein, the term "about" shall refer to a range of tolerance of 10% around a stated value. Therefore, when the term "about" is used to modify a stated value, the range indicated will encompass any number within ±0.01%, 0.02%, 0.05%, 0.1%, 0.2%, 0.5%, 1%, 2%, 3%, 4%, 5%, 6%, 7%, 8%, 9%, or 10% of the stated value.

II. Perfusion Cell Culture

Traditional cell culture involves a "batch" culturing process. In this type of culture, a quantity of fresh medium is inoculated with cells that rapidly enter a logarithmic growth phase. As these cells grow and divide, they consume available nutrients from the medium and excrete harmful waste products. Over time, the culture will enter a stationary growth phase, and finally a decay phase. While modifications to the "batch" culture process have made it more efficient over time, the resultant modified batch culture protocols still result in rapid growth and decay cycles. Furthermore, the "batch" culture process has a limited capacity to reach the levels of cell density that are required to allow for high-density cell banking.

The "fed batch" culture process refers to a further improvement in cell culturing technique over traditional "batch" culture techniques. While this process allows for higher cell density growth, it is still limited in its capacity to allow for efficient growth of high-density cell cultures and, therefore, to efficiently generate cells for high-density cell banking.

In preferred embodiments, the invention employs a perfusion culture process. Perfusion culture is a method for growing cells in which a quantity of fresh medium is inoculated with cells that rapidly enter a logarithmic growth phase (as above) and in which the growth medium is continuously removed from a culture and replaced with fresh medium. In this way, the culture constantly receives fresh medium with high levels of nutrients, while medium containing waste products and with lower levels of nutrients is removed. This type of culturing allows for the maintenance of the logarithmic growth of cells in which at least a half culture volume is exchanged per day and the cell densities can be much higher than those achieved in traditional or modified batch culture (an increase of between 2- to more than 10-fold). In one embodiment of the present invention, the cell specific perfusion rate (CSPR) may be between about 0.02 nL cell$^{-1}$ day$^{-1}$ and about 0.5 nL cell$^{-1}$ day$^{-1}$, e.g. it may be about 0.02 nL cell$^{-1}$ day$^{-1}$, 0.025 nL cell$^{-1}$ day$^{-1}$, 0.05 nL cell$^{-1}$ day$^{-1}$, 0.1 nL cell$^{-1}$ day$^{-1}$, 0.2 nL cell$^{-1}$ day$^{-1}$, 0.3 nL cell$^{-1}$ day$^{-1}$, 0.4 nL cell$^{-1}$ day$^{-1}$, or 0.5 nL cell$^{-1}$ day$^{-1}$. In another embodiment of the present invention, the perfusion rate may be measured in reactor volumes per day and may be between 0 and 15 reactor volumes per day, e.g., it may be about 0 reactor volumes per day, about 0.5 reactor volumes per day, about 1 reactor volume per day, about 2 reactor volumes per day, about 3 reactor volumes per day, about 4 reactor volumes per day, about 5 reactor volumes per day, about 6 reactor volumes per day, about 7 reactor volumes per day, about 8 reactor volumes per day, about 9 reactor volumes per day, about 10 reactor volumes per day, about 11 reactor volumes per day, about 12 reactor volumes per day, about 13 reactor volumes per day, about 14 reactor volumes per day, or about 15 reactor volumes per day. In a specific embodiment, perfusion culture can be carried out in a bioreactor with a minimum of one dip tube.

In certain embodiments, the pH, temperature, dissolved oxygen concentration (DO), and osmolarity of the culture may be adjusted to maximize culture health and productivity. One method of controlling the DO and pH of cultures is through an automated feedback controller. This type of automated controller operates using microprocessor-based computers to monitor and adjust the pH and DO of the culture and thereby maintain optimal conditions for cell growth. However, these automated feedback control systems are costly. Accordingly, in certain embodiments, a non-automated method of controlling these parameters may be employed. In one exemplary embodiment, any of: adjustment of the gas mixture flowing over the culture, adjustment of the WAVE® rock rate, or adjustment of the rock angle of the culture can be used to control selected parameters (e.g. pH or DO). In certain embodiments, both automated feedback control and non-automatic control may be applied.

In one embodiment, the starting level of carbon dioxide gas is at about 10% and the starting level of oxygen gas is at about 20% with an air flow rate of about 0.2 liters per minute (lpm). If the pH is no more than about 6.9, the $CO_2$ set point can be reduced from 10% to 5%. If the pH is still no more than about 6.9 at a later time point, the $CO_2$ set point can be further reduced from 5% to 0%. If the pH is still no more than about 6.9, the perfusion rate can be increased. If the DO is no more than about 45%, the $O_2$ set point should be raised from 20% to 30%. If the DO is no more than about 45% at a later time point, the $O_2$ level should be raised from 30% to 40%, the rock speed should be increased to about 25 rpm, and the rock angle should be changed to about 12°.

i. Cell Culture Media

Any type of cell culture medium suitable for the culturing of cells can be used in the methods of the present invention. Guidelines for choosing an appropriate cell medium are well known in the art and are provided in, for example, Chapters 8 and 9 of Freshney, R. I. Culture of Animal Cells (a manual of basic techniques), 4th edition 2000, Wiley-Liss; and in Doyle, A., Griffiths, J. B., Newell, D. G. Cell & Tissue Culture: Laboratory Procedures 1993, John Wiley & Sons. Each of these references is hereby incorporated in its entirety. There are further methods in the art for the preparation and maintenance of cell cultures under animal derived component-free and protein-free conditions (including methods concerning CHO cells) such as those seen in International Patent Application No. WO97/05240, No. WO 96/26266, and No. WO 00/11102, and U.S. Pat. No. 6,100,061, 6,475,725, and 8,084,252. Each of the preceding documents is hereby incorporated by reference in its entirety. In one embodiment of the present invention, animal-derived component (ADC)-free medium can be used. Conventional synthetic minimal media may contain inorganic salts, amino acids, vitamins, a carbohydrate source, and water. In a specific embodiment of the present invention, the medium that may be used is CD-CHO (GIBCO, Invitrogen Corp.; an animal origin-free medium that is chemically defined and contains no proteins, hydrolysates, or components of unknown origin). Additionally, the medium may have additional components including glutamine and/or methotrexate or other factors which may aid in growth or adherence. In a specific embodiment, the additional component may be GLUTAMAX-1 or L-glutamine added at between about 2 mM and about 8 mM, e.g., at about 2 mM, about 3 mM, about 4 mM, about 5 mM, about 6 mM, about 7 mM, or about 8 mM.

ii. Host Cells and Expression Vectors

In certain embodiments, the cells employed in the cell banking process of the invention are host cells harboring an expression construction for expression of a therapeutically relevant protein or other polypeptide of interest. Any cell that can be used to express a polypeptide of interest (e.g., a binding polypeptide) can be used according to the methods described herein. The cells may optionally contain naturally occurring or recombinant nucleic acid sequences, e.g. an expression vector that encodes a polypeptide of interest. The expression vector may optionally contain appropriate transcriptional and translational controls and may be constructed using recombinant DNA technology known in the art. Expression vectors may be transferred to any host cell by techniques known in the art, and the transformed cells may then be cultured according to the method of the present invention to create a high-density cell bank. Furthermore, the high-density cell bank may then be thawed and cultured according to techniques known in the art in order to produce the encoded protein of interest and, where desired, this protein may be subsequently purified.

In certain embodiments, a variety of host expression systems can be used to produce therapeutically relevant proteins. Furthermore, the host expression system may be a mammalian cell system (e.g., CHO, CHO-DBX11, CHO-DG44, CHO-S, CHO-K1, Vero, BHK, HeLa, COS, MDCK, HEK-293, NIH-3T3, W138, BT483, Hs578T, HTB2, BT20, T47D, NS0, CRL7030, HsS78Bst cells, PER.C6, SP2/0-Ag14, and hybridoma cells) harboring recombinant expression constructs containing promoters derived from the genome of mammalian cells. Viral-based expression systems can also be utilized in concert with mammalian cells (see, e.g., Logan et al, 1984, Proc. Natl. Acad. Sci. USA 8:355-359, hereby incorporated by reference in its entirety). The efficiency of expression can be enhanced by the inclusion of elements including (but not limited to) appropriate transcription enhancer elements and transcription terminators (see, e.g., Bittner et al., 1987, Methods in Enzymol. 153:516-544, hereby incorporated by reference in its entirety).

In other embodiments, a host cell strain can be chosen that modulates the expression of the inserted sequences or that modifies and processes the gene product in the specific fashion desired. Different host cells have characteristic and specific mechanisms for the post-translational processing and modification of proteins and gene products. Appropriate cell lines or host systems can be chosen to ensure the correct modification and processing of the polypeptide (e.g., a binding polypeptide) expressed. Such cells include, for example, established mammalian cell lines and animal cells, as well as insect cell lines, fungal cells, and yeast cells.

iii. Bioreactors

Any bioreactor suitable for culturing cells under perfusion culture conditions may be employed in the methods of the invention. The bioreactor may be inoculated using an aliquot of cells at an appropriate seed density (such as a vial of cells or cells from a starter culture, e.g. a shake flask or a shake flask seed train that have been cultured to that density). The appropriate seed density for a culture depends on several factors including the type of cells used and the bioreactor being inoculated. The appropriate seed density can be determined using methods available in the art.

In certain embodiments, the bioreactor may be of a disposable nature, for example the bioreactor can be a flexible bag or a plastic flask that is connected to the cell retention device by means of flexible tubing. The design may include, but is not required to include, an inlet conduit and an outlet or inoculation conduit, which can be sterilely welded or connected to the source of the eukaryotic cells. In certain embodiments, the bioreactor has a volume of at least about 1 L, e.g., about 1 L, 2 L, 5 L, 10 L, 20 L, 50 L, 75 L, 85 L, 100 L, 150 L or 400 L. In a specific embodiment of the invention, the bioreactor is a 10 L flexible bag that has been customized with one or two dip tubes that are used to remove medium or product. Exemplary disposable bioreactors are WAVE® cell bag bioreactors (GE Healthcare, Pittsburgh, PA) such as the 20 L WAVE® bioreactor. These are the perfusion bioreactor systems described in, among other documents: Singh, 1999, Disposable bioreactor for cell culture using wave-induced agitation, Cytotechnology, p. 149-158, hereby incorporated by reference in its entirety.

The working volume of the reactor is the volume occupied by culture. The working volume can be, for example, about 10%, 20%, 30%, 40%, 50%, 60%, 70% or more of the culture, but preferably not more than about 75%.

Alternatively, the bioreactor may be of a non-disposable nature. For example, the bioreactor can be made of stainless steel or glass. Alternative bioreactors suitable for use in the present invention include, but are not limited to: shake flasks, stirred tank vessels, airlift vessels, and disposable bags that can be mixed by rocking, shaking, or stirring.

In an embodiment, the bioreactor may be coupled to a cell retention system, including, but not limited to, built-in filters, spin baskets, tangential flow filtration (TFF) systems, and alternating tangential flow filtration (ATF) systems.

III. Cell Retention

Perfusion culture depends on the ability to remove nutrient-depleted and waste product-containing media from the culture while minimizing damage to the cells. Initial methods of cell retention, in which the depleted medium was separated from cultured cells, frequently damaged the cells through, for example, the creation of shear forces. This cell damage resulted in the clogging of filters and the failure of the perfusion devices, many of which were internal to the culture system. Accordingly, in one aspect, the current disclosure provides a method that makes use of a "cell retention system" that allows for media exchange.

In one embodiment, the type of cell retention system used is a "built-in" type filter, wherein the filter is disposed in the chamber of the bioreactor and is free to move within the chamber. The filter may be coupled to one of the tubes leading out of the chamber, thereby allowing filtered medium to be drawn from the culture. One example of a "built-in" type filter may be found in U.S. Pat. No. 6,544,788, which is hereby incorporated by reference in its entirety.

In another embodiment, the cell retention system used is a tangential flow filtration system (TFF). In a TFF system, culture medium is circulated from a culture vessel through a filtration module, and then back to the culture vessel by means of a pump attached to the tubing between the filtration module and the culture vessel, producing a tangential flow across the filter module. A second pump is positioned on the filtrate side of the filter module and is used to control the rate at which filtrate is removed. The use of hollow-fiber membrane filters is preferred in this system as they are easier to sterilize and allow for the maintenance of a uniform flow across the filter module. However, when hollow fiber filters are employed in this system, they are prone to clogging as the mono-directional flow leads to the aggregation of particulate matter at the lumen inlet.

In a specific embodiment, the type of cell retention system used is an alternating tangential flow (ATF) system. In the ATF type of cell retention system, a filtering compartment is connected to a storage vessel at one end and a diaphragm pump at the other. The pump first moves medium from the vessel through the filter element to the pump and then reverses to send the medium from the pump through the filter and back to the vessel, creating a bi-directional or alternating flow. This is referred to as alternating tangential flow (ATF) as there is alternating tangential flow at the filter module, i.e., there is one flow in the same direction to the membrane surfaces of the filter module (tangential to that surface), and that there is another flow that is substantially perpendicular to those surfaces. This type of filtration has been extant in the literature since 2000 and results in rapid, low shear, uniform flow. ATF filtration can be obtained by methods known in the art, such as are described in U.S. Pat. No. 6,544,424, which is hereby incorporated by reference in its entirety. Furthermore, alternating tangential flow systems are available commercially from manufacturers such as Refine Technology and include various models such as the ATF2, ATF4, ATF6, ATF8, and ATF10 systems, In another specific embodiment of the invention, the filter is a tubular membrane filter, and furthermore may be a hollow fiber filter.

As indicated above, the methods of the invention allow for efficient growth of cells to ultra-high densities. In a particular embodiment of the invention, the culture is grown to a density of at least about $1 \times 10^8$ cells/mL, e.g. to about $1 \times 10^8$ cells/mL, about $1.1 \times 10^8$ cells/mL, about $1.2 \times 10^8$ cells/mL, about $1.3 \times 10^8$ cells/mL, about $1.4 \times 10^8$ cells/mL, about $1.5 \times 10^8$ cells/mL, about $1.6 \times 10^8$ cells/mL, about $1.7 \times 10^8$ cells/mL, about $1.8 \times 10^8$ cells/mL, about $1.9 \times 10^8$ cells/mL, or about $2 \times 10^8$ cells/mL. Growth of the culture to these high concentrations allows immediate cryopreservation of high-density stocks without further concentration of the cell population through centrifugal or non-centrifugal methods.

IV. Cryopreservation and Cell Banking

Cryopreservation refers to a process by which cells, tissues, or any other substances susceptible to damage caused by time or by enzymatic or chemical activity are preserved by cooling and storing them at sub-zero temperatures. The importance of cryopreservation of important cell lines cannot be underestimated, as (among other important advantages) this allows the maintenance of these lines without maintaining them in constant culture, decreases the risk of contamination, and reduces the risk of genetic drift.

When using cryopreservation methods, it is vital to reach and stay at these low temperatures without causing additional damage through the formation of ice during the freezing process. Methods in the art traditionally use substances that decrease freezing damage to cells called cryoprotectants. Cryoprotectants may be added to the medium of cell cultures prior to the freezing process. In a specific embodiment, the cryoprotectant used may be one or more of: glycerol or dimethyl sulphoxide (DMSO). Additionally, the cryoprotectant may be added with or without hydroxyethyl starch (HES). In a further specific embodiment, DMSO may be added at a concentration of at least about 5%, e.g. it may be added at about 5%, about 6%, about 7%, about 8%, about 9%, about 10%, about 11%, about 12%, about 13%, about 14%, about 15%, about 16%, about 17%, at about 18%, about 19%, or at about 20%.

The culture with added cryoprotectant may then be dispensed into containers appropriate for storage under cryopreservation conditions. In one embodiment, this container may be a vial made of a material which may include (but is not limited to) polymers such as polytetrafluoroethylene, polystyrene, polyethylene, or polypropylene. In a specific embodiment, the vial may have an additional surface treatment in order to improve cryopreservation conditions (e.g., hydrophilic coatings which reduce adsorption and denaturation). In exemplary embodiments, the vial may have a volume of more than about 0.1 mL, e.g. the vial may have a volume of about 0.1 mL, about 0.5 mL, about 0.75 mL, about 1 mL, about 1.5 mL, about 2 mL, about 2.5 mL, about 4.5 mL, about 10 mL, about 15 mL, about 20 mL, about 25 mL, or about 50 mL. In another embodiment, the container may also be a cryobag having a volume of more than about 30 mL, e.g. the cryobag may have a volume of about 30 mL, about 50 mL, about 100 mL, about 150 mL, about 200 mL, about 300 mL, about 400 mL, or about 500 mL. The cryobag may be constructed of any appropriate material including, but not limited to, polymers such as polytetrafluoroethylene, polystyrene, polyethylene, polypropylene, Fluorinated Ethylene Propylene (FEP), polyolefin, and ethylene vinyl acetate (EVA). Exemplary disposable bioreactors include but are not limited to: KryoSure® Cryopreservation bags, PermaLife™ Bags (OriGen Biomedical), CryoStore freezing bags (OriGen Biomedical), Freeze-Pak™ Biocontainers (Charter Medical), and bags disclosed in U.S. Provisional Application No. 62/037,181 (Merial Ltd., a Sanofi company), which is incorporated by reference herein in its entirety.

These containers are then frozen using techniques and devices well known in the art before being stored at low temperatures, typically between about −130 t and about −196° C. In one embodiment the freezing technique used may be control-rate and slow freezing (also called slow programmable freezing, or SPF). The collection of cells obtained by the process is a cell bank.

In an embodiment, the cell bank may be, but is not limited to, an ultra-high density cell bank, a master cell bank, a working cell bank, or a mini bank.

V. Determination of Cell Viability

As indicated above, the methods of the invention allow for cell banking at high densities while retaining excellent cell viability for later use. As used herein, the term "cell viability" can be defined as the number or percentage of healthy cells in a given sample. The viability of cells may be determined using any method available in the art at any point in the ultra-high density cell banking process described. Commonly used methods for the determination of cell viability are largely based on the principle that live cells possess intact cell membranes that exclude certain dyes, such as trypan blue (a diazo dye), Eosin, or propidium, whereas dead cells do not.

In one embodiment, trypan blue can be used to stain a quantity of cells and thereby indicate the presence of cells with intact membranes (not colored) and the presence of cells with disrupted membranes (blue). These cells may then be counted to determine the numbers of both live and dead cells in the culture, and presented as a percentage to indicate the relative health of the culture.

In a specific embodiment the cell viability may be determined using a culture that has been grown to an ultra-high density, but has not yet been frozen (i.e. a pre-freezing or pre-thaw culture). In a specific embodiment the cell viability may be determined using a culture that has been frozen and then thawed (i.e., a post-freezing or post-thaw culture).

In a specific embodiment, the cell viability is at least about 60%, e.g. about 60%, about 65%, about 70%, about 75%, about 80%, about 85%, about 90%, or about 95%. In certain embodiments, the post-thaw viability of the cells is at least about 80%, e.g., is at least about 85%, 90%, or 95% including up to 100%.

VI. Therapeutically Relevant Proteins

Cells derived from the ultra-high density cell cryobanking method of the invention can be employed in a later production phase for the manufacture of a protein. For example, the cells propagated in the bioreactor and frozen in high-density bank aliquots according to the methods of the present invention may be used for the production of biological substances including therapeutically relevant proteins. These biological substances may include, but are not limited to: viruses (see e.g. WO200138362), binding polypeptides such as antibodies, e.g. monoclonal antibodies, and fragments thereof, e.g., Fab fragments; Fc fusion proteins, anticoagulants, blood factors, bone morphogenetic proteins, engineered protein scaffolds, enzymes, growth factors, hormones, interferons, interleukins, and thrombolytics. These biological substances can be harvested using any method available in the art. In one embodiment, the invention provides a method of producing a biological substance, the method comprising: culturing cells capable of expressing a biological substance under conditions suitable for the production of a biological substance, wherein the cells were obtained from an ultra-high density frozen cell bank produced using perfusion culture. The biological substance may be (but is not limited to) a protein (e.g., any therapeutically relevant protein).

EXAMPLES

The present invention is further illustrated by the following examples which should not be construed as further limiting. The contents of the figures and all references, patents, and published patent applications cited throughout this application are expressly incorporated herein by reference in its entirety.

Example 1: General Methods

The following conditions were common to the experiments set forth in Examples 3-6 below.

The pH set point was 7.0±0.1. The pH of the culture was kept at the set point through automatic feedback control by a WAVE POD controller. The automatic controller changed $CO_2$ concentration in the gas to the headspace and further regulated the addition of base ($CO_2$/base control scheme). When the controller detected a pH below the selected pH set point, an attempt was first made to reach the set pH value by lowering the $CO_2$ level. If the requested pH level was not reached within the specified time, base was added. At a pH above the selected pH set point, the $CO_2$ concentration was increased.

The DO (dissolved oxygen) set point was ≥40%. The DO of the culture was kept at the set point through automatic feedback control by a WAVE POD controller. Oxygen concentration was automatically altered from 21% to 50% ($O_2$ concentration control scheme). Additional pure oxygen gas was supplied manually to the headspace in combination with manual adjustments to the rocking condition in order to keep DO≥40%. Specifically, when the online DO was approximately 40%, and $O_2$ concentration from the POD controller was increased from 21% to >30%, the wave rock speed and angle were increased from 22 rpm/10° to 25 rpm/12°. If the POD $O_2$ became >30% again, the wave rock speed and angle were increased from 25 rpm/12° to 30 rpm/12° or pure $O_2$ was supplied to the headspace (the latter being preferred). Finally, the volume percentage of pure $O_2$ in the gas was gradually increased to increase the total $O_2$ to the headspace. The manual addition strategy resulted in an increase of approximately 10% per day by adjusting the volume control ratio between the POD oxygen gas (21%-50%, supplied by the POD controller) and the additional pure oxygen gas (100%, controlled by a rotameter). The total gas flow rate was increased slightly in order to facilitate gas transfer.

The CSPR (cell specific perfusion rate) of the cultures was kept almost constant by increasing the perfusion rate daily based on the measured cell density.

Example 2: Design and Implementation of an Ultra-High Density Cell Banking Protocol This ultra-high density cell cryobanking protocol begins with a 2-mL master cell bank vial of cells (working volume 1.5 mL) at an approximate density of $2.0-2.4\times10^7$ viable cells/mL (normal cell cryopreservation condition). Subsequently, the cells are grown in perfusion culture. Following the addition of DMSO to the cell culture, this ultra-high density cell culture is dispensed into separate 5-mL vials (approximately 4.5 mL working volume) or cryobags (approximately 100 mL working volume) appropriate for cryopreservation and storage as an ultra-high density cell bank (at least about $10\times10^7$ cells/mL). A schematic representation of this protocol is shown in FIG. 1.

Example 3: Ultra-High Density Cell Culture and Cell Bank Performance Using rCHO 1

Figure 2:
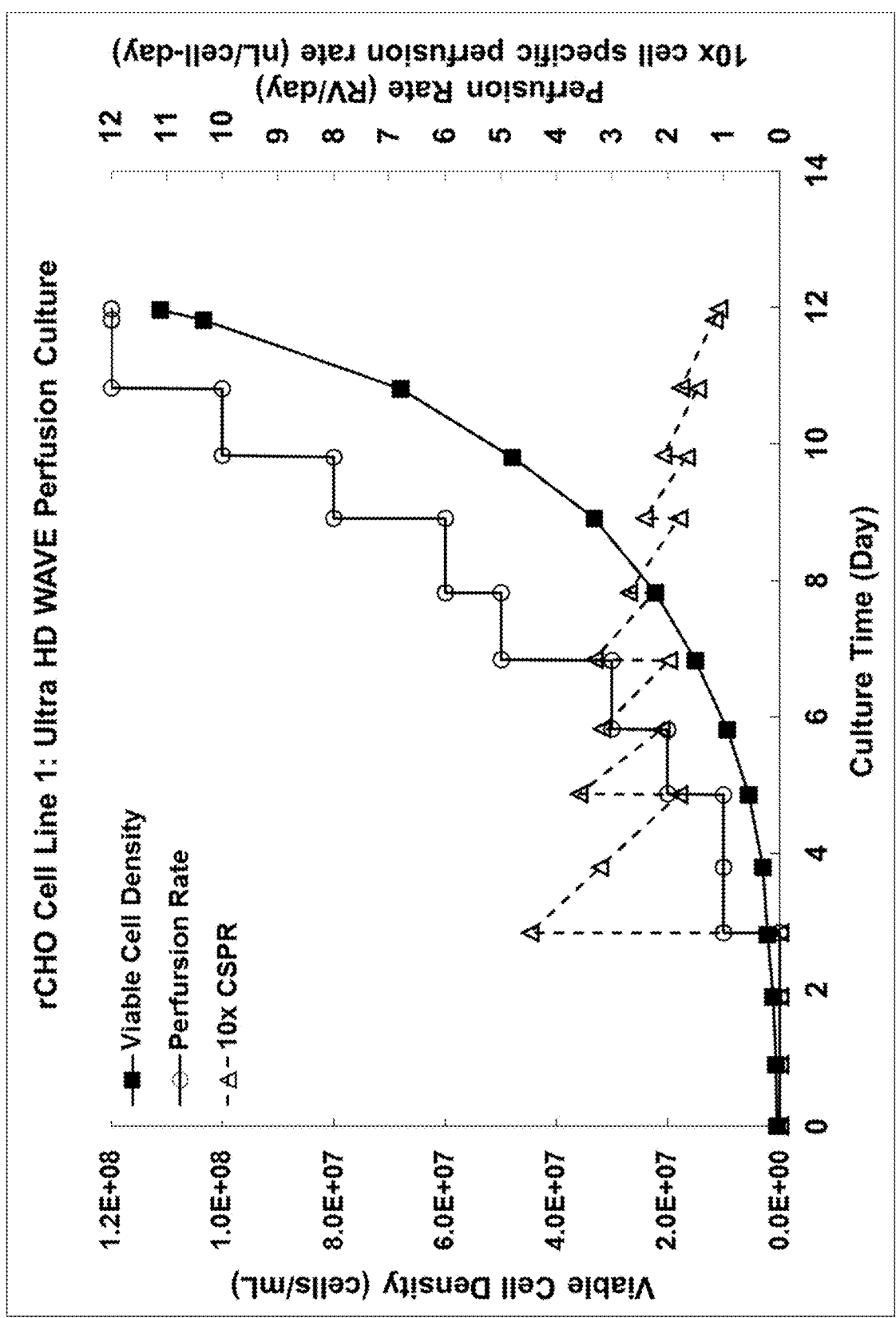
FIG. 2: is a graph depicting the viable cell density (cells/mL), perfusion rate (RV/day) and 10× cell specific perfusion rate (nL/cell-day) in an exemplary culture of rCHO cell line 1.
Figure 3:
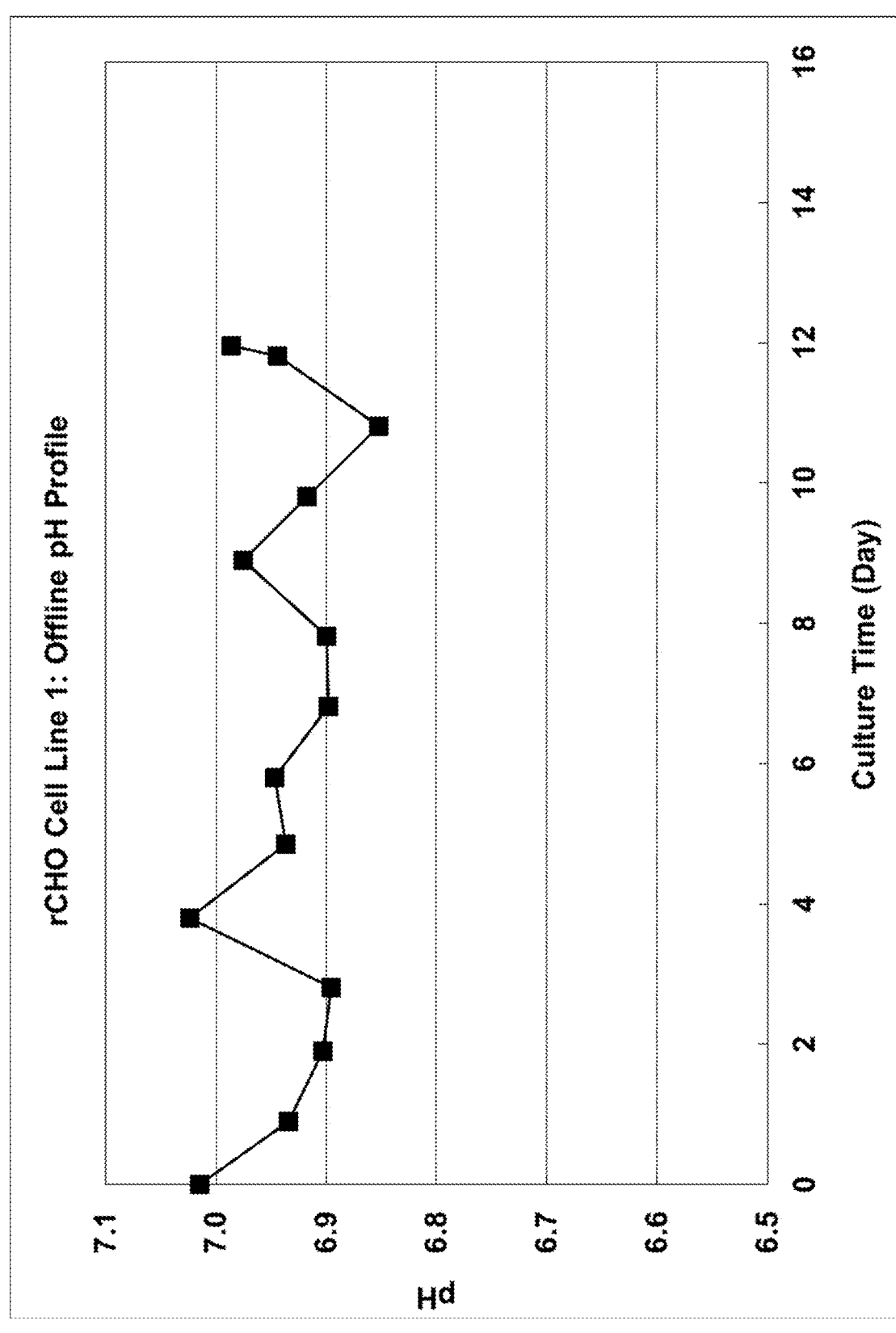
FIG. 3: is a graph depicting the offline pH profile in a culture of rCHO cell line 1.
Figure 4A:
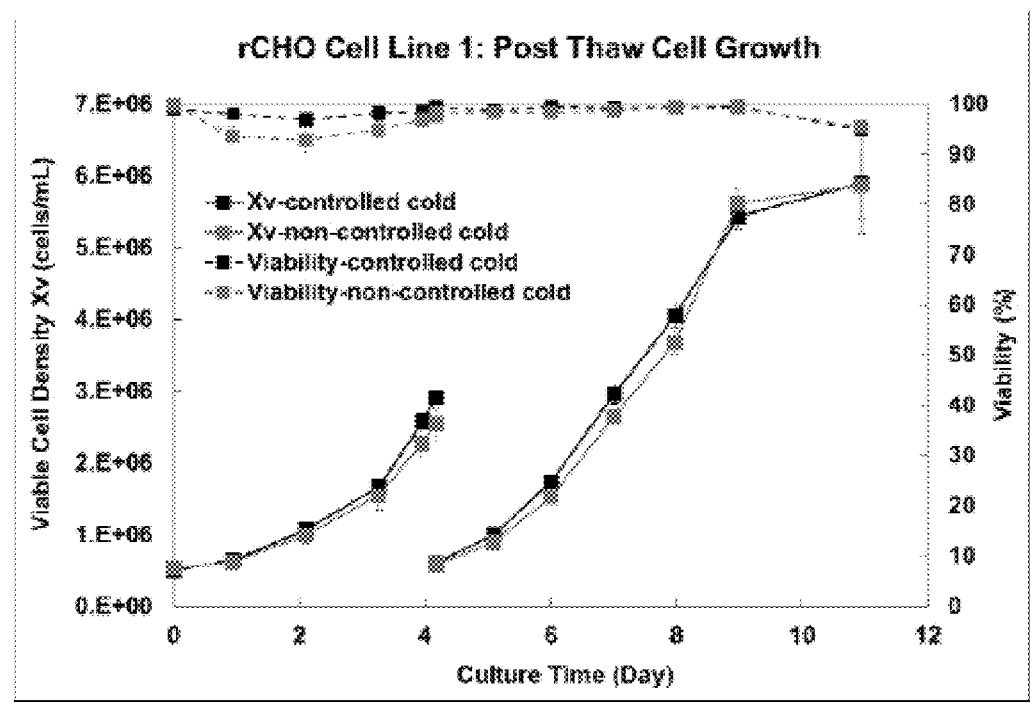
FIGS. 4A-4C: are a series of graphs depicting (FIG. 4A) the post-thaw cell growth profile, (FIG. 4B) the percentage of post-thaw late apoptotic cells, and (FIG. 4C) the specific production rate (units/E9 cells-day) for a 5-mL ultra-HD cell bank aliquot of rCHO cell line 1.
Figure 4B:
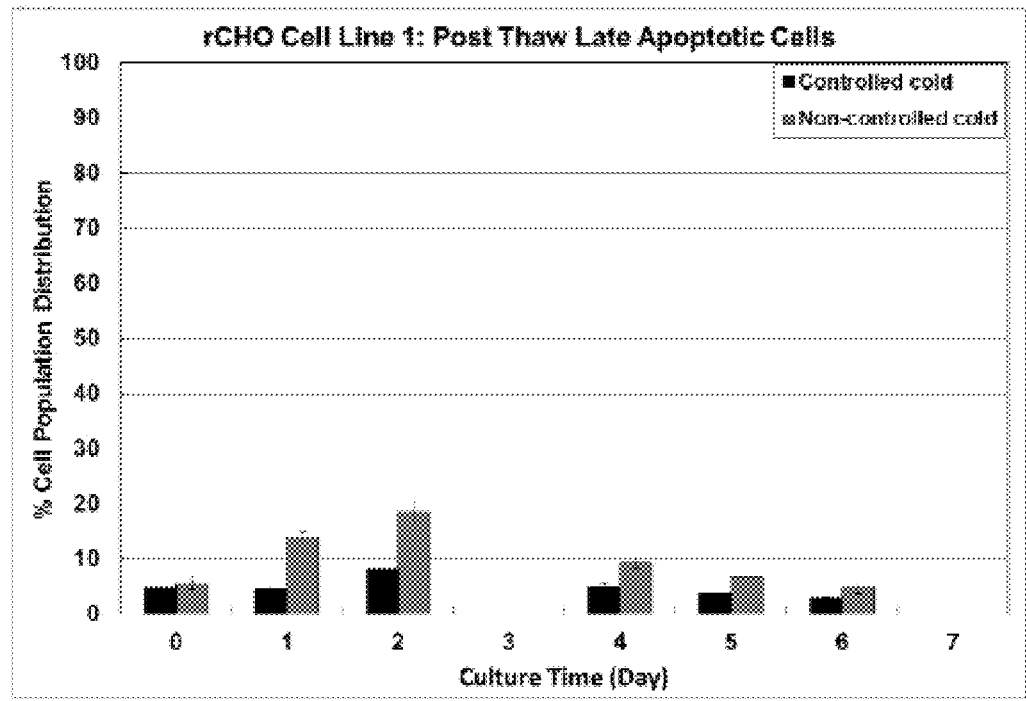
Figure 4C:
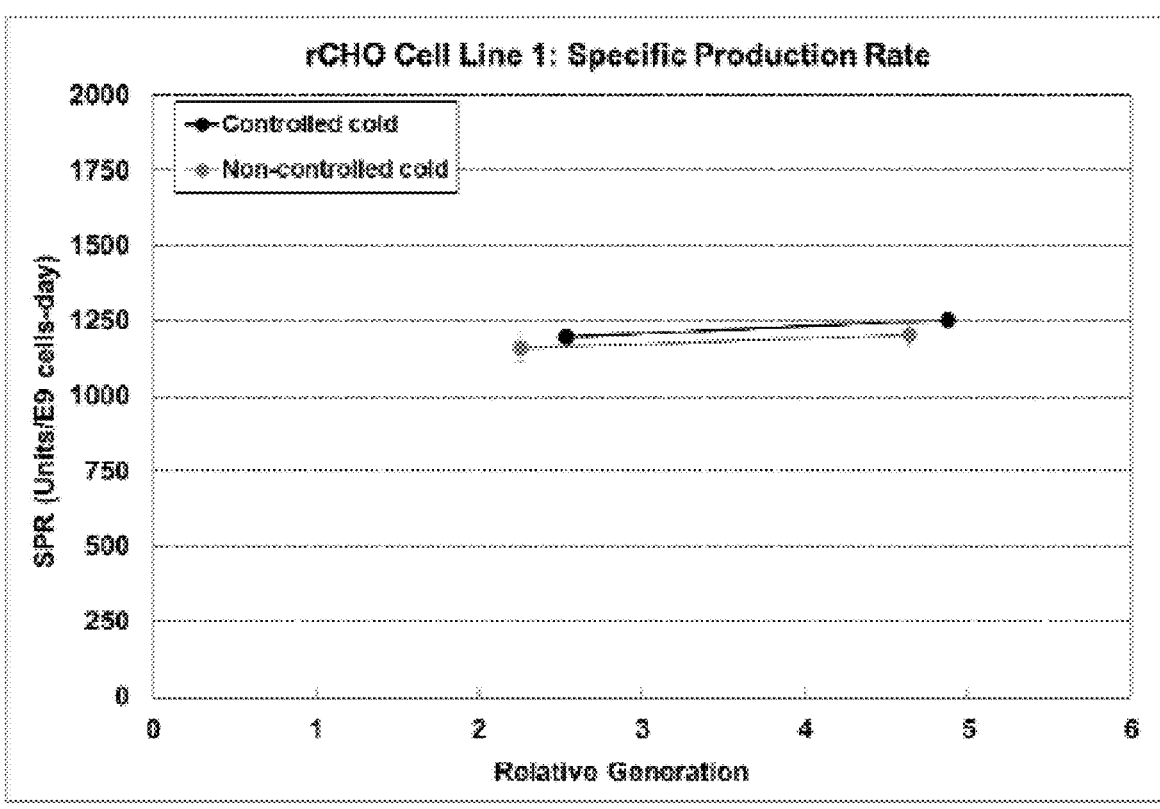

The parameters for the following experiment were as follows:
1) $CO_2$ was decreased to 0% when Xv≥about $3\times10^7$ viable cells/mL (vc/mL) (on day 9), base was then added afterwards when needed;
2) WAVE rock speed & angle: initially 22 rpm/10° (from day 0 to day 8); increased to 25 rpm/12° when POD $O_2$ increased from 21% to >30% (on day 8), and then to 30 rpm/12° (on day 9) to facilitate gas transfer (supplying $O_2$ and removing $CO_2$);

3) Additional pure $O_2$ (100%): supplied manually to the headspace when POD $O_2$>30% and Xv≥about $6\times10^7$ vc/mL (on day 11);
4) Total gas flow rate: 0.2 lpm (liters per minute) from day 0 to day 10, increased to 0.4 lpm on day 10 when Xv>$4\times10^7$ vc/mL, and then to about 0.5 lpm on day 11 (POD $O_2$: pure $O_2$=3:1, total $O_2$: about 62%); and
5) Cell specific perfusion rate: target at ≥about 0.2 nL/cell-day initially; perfusion rate was increased step-wise up to 12 RV/day (note: RV is defined as reactor volume). The CSPR on the final day was between 0.1 nL/cell-day and 0.2 nL/cell-day.
6) Seed train and Bioreactor medium: CD CHO with 4 mM L-glutamine
7) Bioreactor: GE custom 10-L Cellbag perfusion bioreactor with two dip tubes; working volume: 5 L;
8) Bioreactor inoculum: shake flask seed train; seed density: about $5\times10^5$ vc/mL
9) Cell retention methods: ATF4 (0.2 μm pore size)
10) Temperature of cell culture: 37° C.
11) Freeze down: CryoMed™ controlled-rate freezer Ultra-high density (UHD) cell culture and cell bank performance (post-freezing and thaw) were tested for rCHO cell line 1. The perfusion culture reached Xv of about $1.11\times10^8$ vc/mL on day 12 with high viability (>97% throughout the whole process). The viable cell density (cells/mL), perfusion rate in reactor volumes/day, and 10×CSPR (10× cell specific perfusion rate in nL/cell-day) of the ultra-high density perfusion culture are shown in FIG. 2. FIG. 3 shows the offline pH profile of the culture. The culture was harvested directly without concentration to generate two UHD banks in 5-mL vials at two DMSO holding temperatures: well-controlled cold temperature using a 4° C. jacketed spinner and non-controlled cold temperature using a spinner chilled by an ice water bath. FIGS. 4A-4C show the post freezing performance of 5 mL UHD vials created from the aforementioned cell culture conditions. Both UHD banks had rapid post-freezing cell growth, very high viability, and a low rate of apoptosis. However, the more active control of temperature in the jacked spinner resulted in a slightly improved post bank recovery and growth when compared to more passive temperature control in the ice water bath.

Example 4: Ultra-High Density Cell Culture and Cell Bank Performance Using rCHO 2

The parameters for the following experiment were as follows:
1) $CO_2$ was decreased to 0% when Xv≥about $5\times10^7$ vc/mL (on day 9), base was then added afterwards when needed.
2) WAVE rock speed & angle: initially 22 rpm/10° (from day 0 to day 7); increased to 25 rpm/12° when POD $O_2$ increased from 21% to >30% (on day 7) to facilitate gas transfer (for supplying $O_2$ and removing $CO_2$).
3) Additional pure $O_2$ (100%) was supplied manually to the headspace when POD $O_2$>30% and Xv≥about $3\times10^7$ vc/mL (on day 8).
4) Total gas flow rate was 0.2 lpm initially (from day 0 to day 8), and increased to 0.4 lpm on day 8 when Xv≥about $3\times10^7$ vc/mL (POD $O_2$: pure $O_2$=3:1, total $O_2$: about 62%), and then to about 0.5 lpm on day 9 (POD $O_2$: pure $O_2$=1:1, total $O_2$: about 75%).
5) Cell specific perfusion rate: target at ≥about 0.2 nL/cell-day in the beginning, but perfusion rate was increased stepwise up to 12 RV/day. On the last day, 0.1 nL/cell-day<CSPR<0.2 nL/cell-day.

6) Seed train and Bioreactor medium: CD CHO with 4 mM L-glutamine

7) Bioreactor: GE custom 10-L Cellbag perfusion bioreactor with one dip tube; working volume: 5 L;

8) Bioreactor inoculum: shake flask seed train; seed density: about $5\times10^5$ vc/mL 9) Cell retention methods: ATF4 (0.2 μm pore size)

10) Temperature of cell culture: 37° C.

11) Freeze down: CryoMed™ controlled-rate freezer

Figure 5:
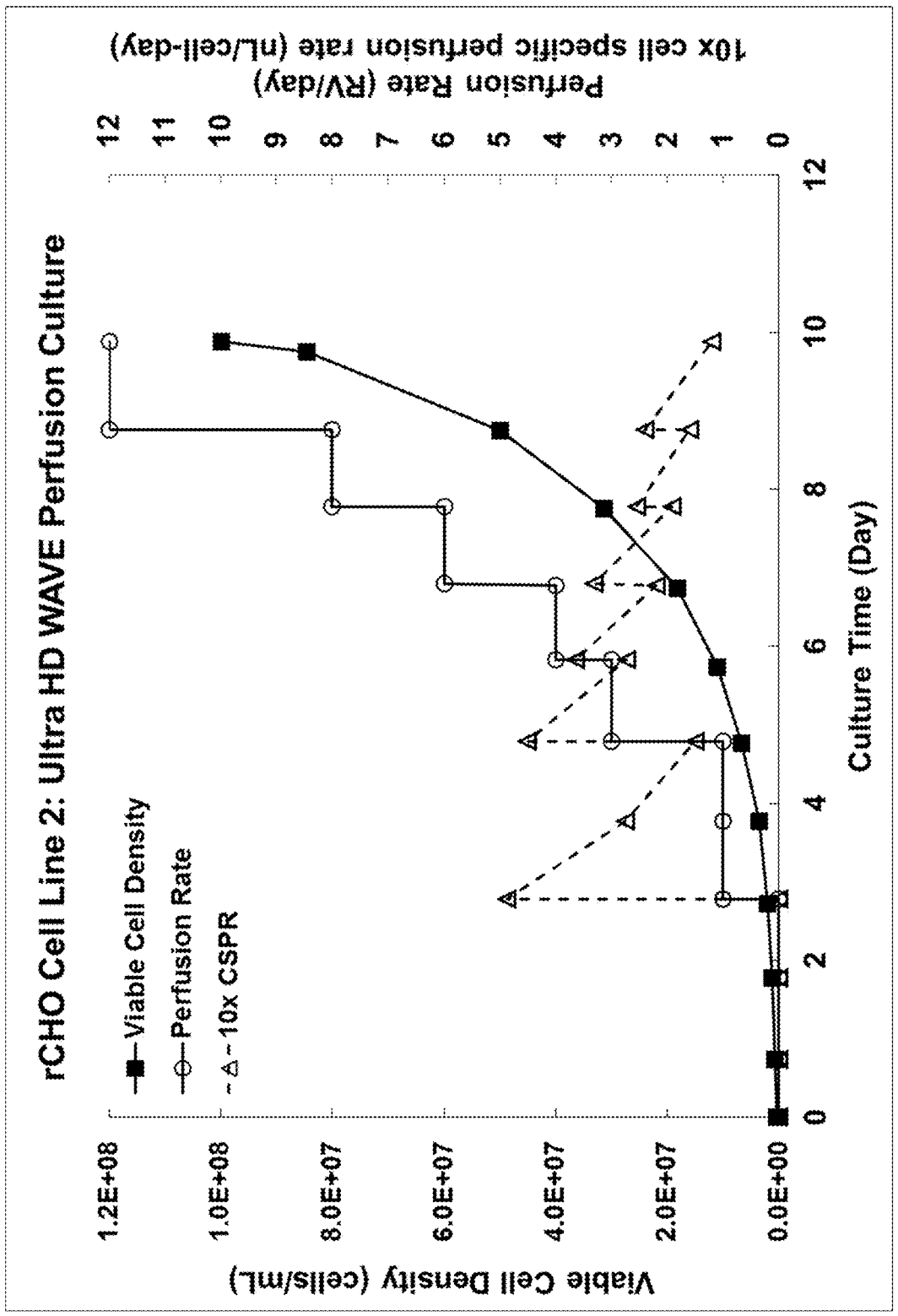
FIG. 5: is a graph depicting the viable cell density (cells/mL), perfusion rate (RV/day) and 10× cell specific perfusion rate (nL/cell-day) in an exemplary culture of rCHO cell line 2.
Figure 6:
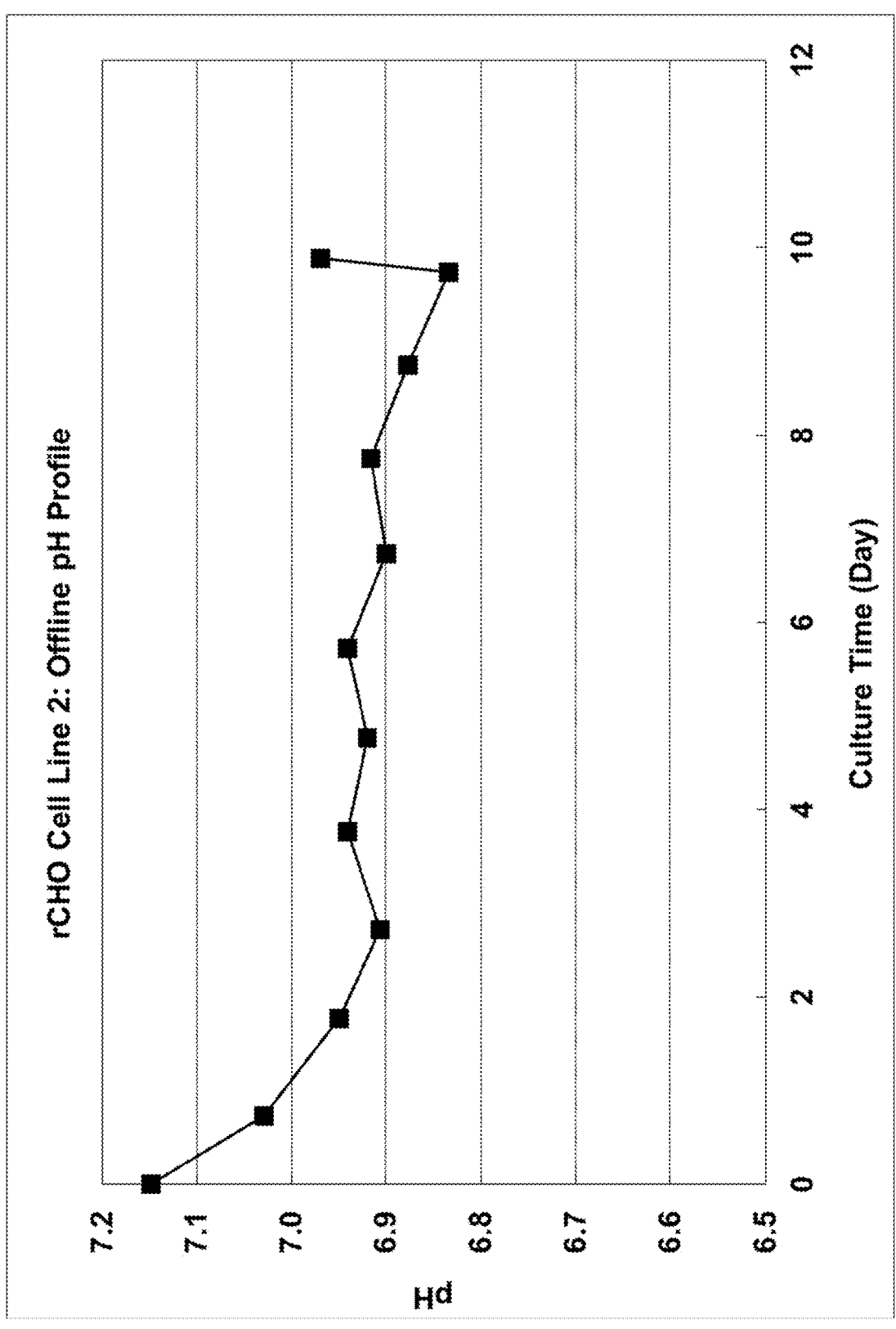
FIG. 6: is a graph depicting the offline pH profile in a culture of rCHO cell line 2.

Ultra HD cell culture and cell bank performance (post-freezing and thaw) were tested for rCHO cell line 2. The viable cell density (cells/mL), perfusion rate in reactor volumes/day, and 10×CSPR (10× cell specific perfusion rate in nL/cell-day) for the ultra-high density perfusion culture are shown in FIG. 5. FIG. 6 shows the offline pH profile of the culture. The culture was harvested to make UHD (ultra-high density) 5-mL vials and 100 mL UHD cryobags for cryopreservation at two different DMSO holding conditions: 1) room temperature (RT, approximately 22-25° C.); and 2) a controlled cold temperature (CT, approximately 5° C. using a 4° C. jacketed spinner).

Figure 7:
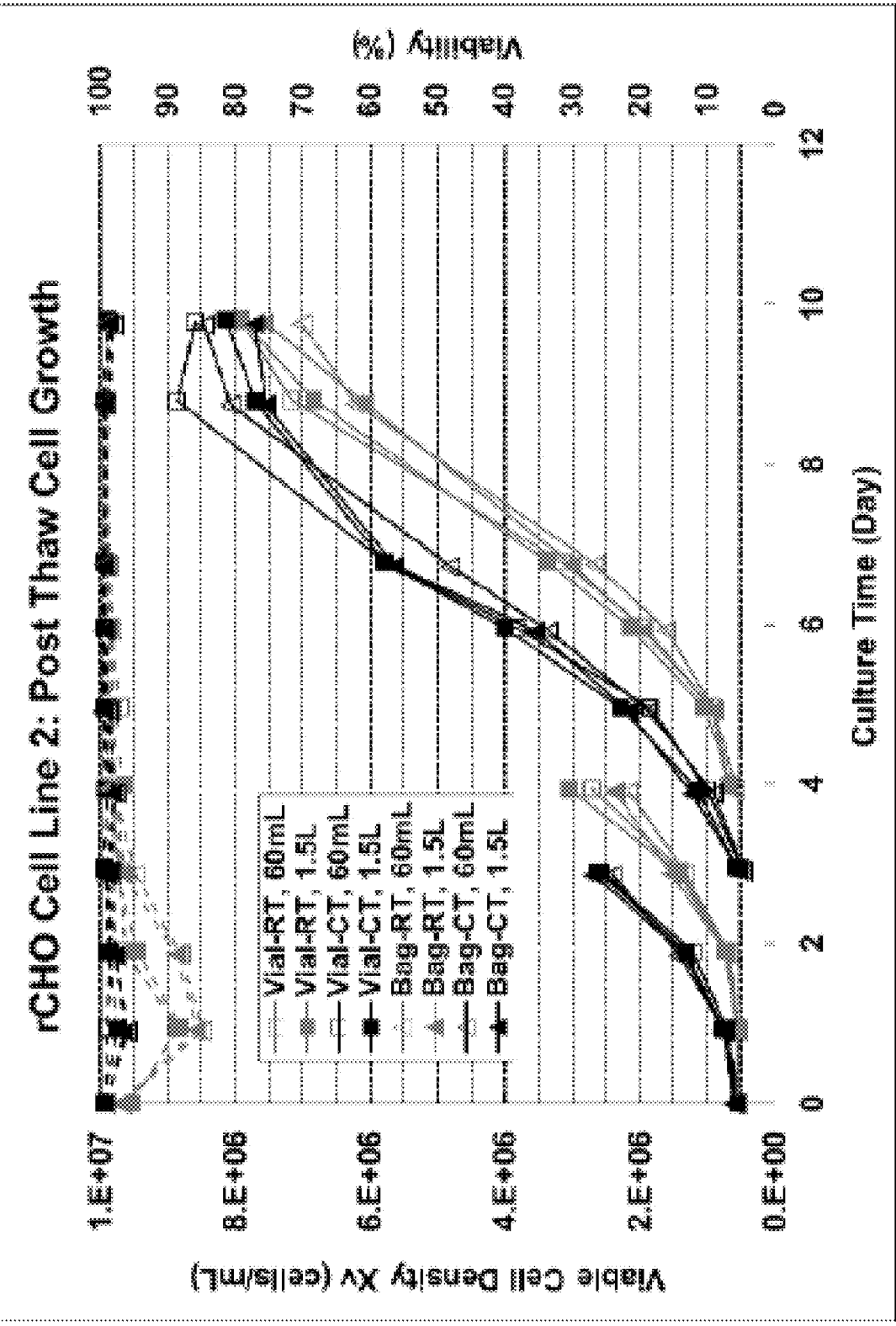
FIG. 7: is a graph depicting the cell growth based on viable cell density Xv (cells/mL; solid lines) and viability (dotted lines) for rCHO cell line 2 when seeded at $0.5 \times 10\string^6$ vc/mL in 250-mL and 3-L shake flasks.
Figure 8:
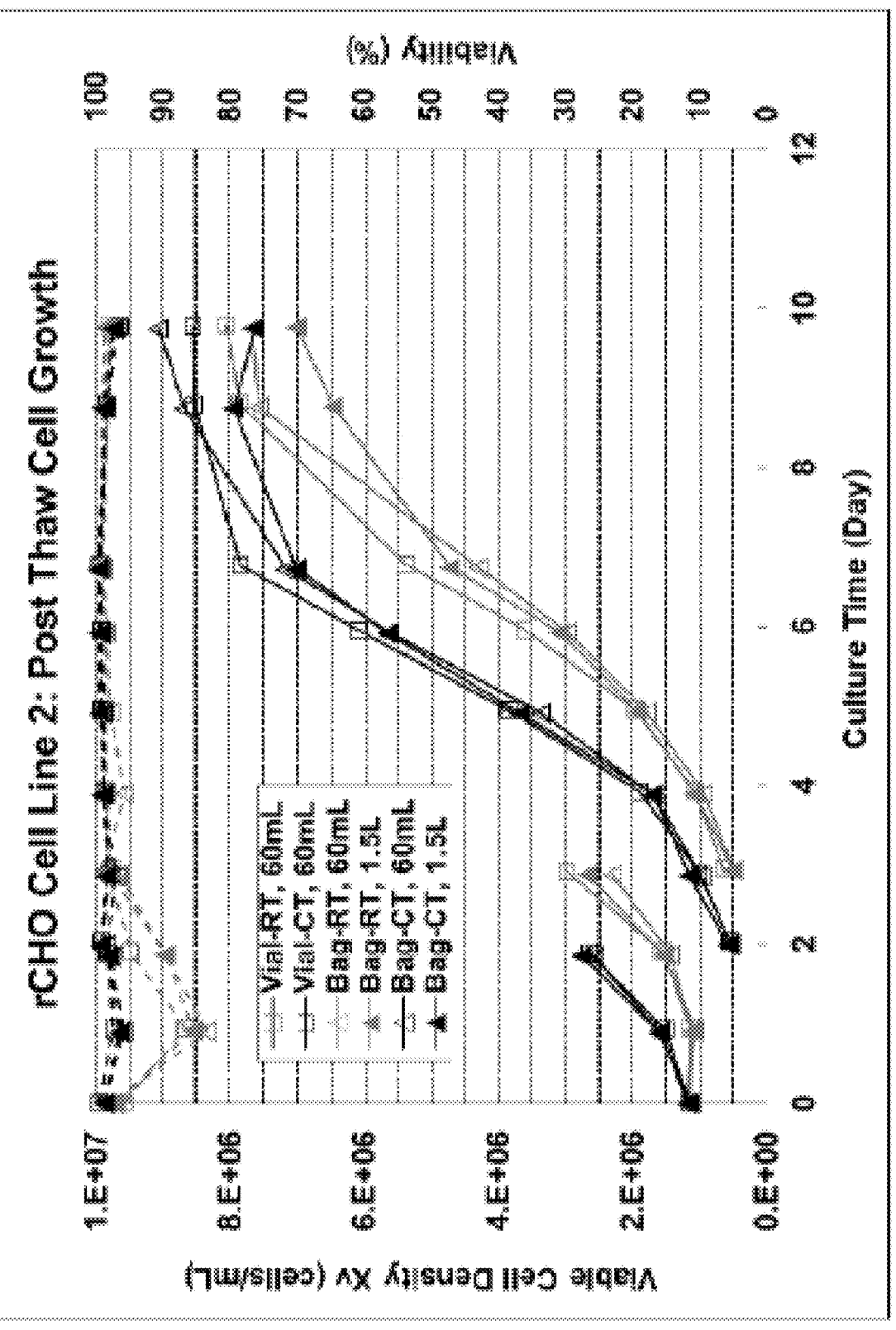
FIG. 8: is a graph depicting the cell growth based on viable cell density Xv (cells/mL; solid lines) and viability (dotted lines) for rCHO cell line 2 when seeded at $1.0 \times 10\string^6$ vc/mL in 250-mL and 3-L shake flasks.
Figure 9:
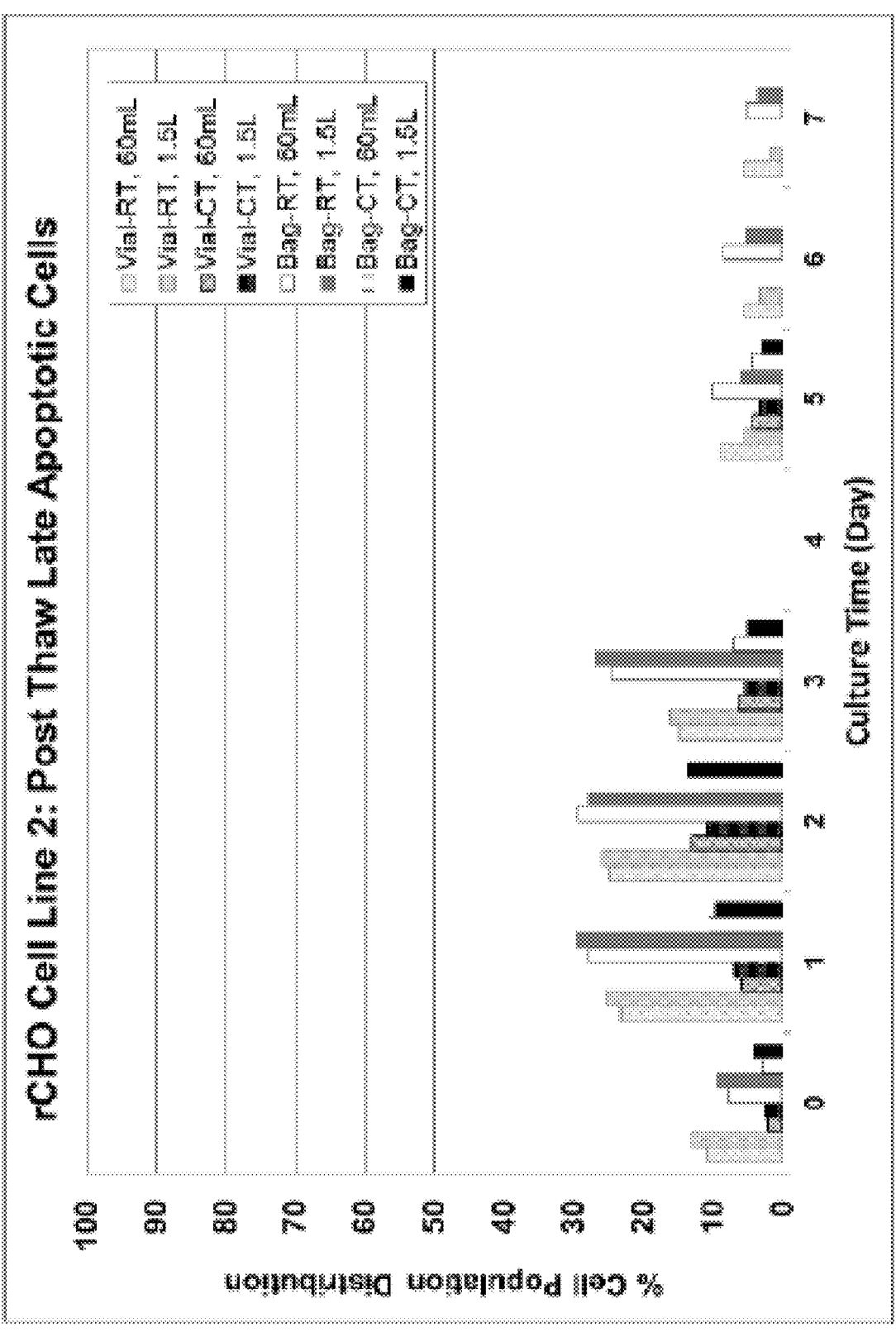
FIG. 9: is a graph depicting the percentage of late apoptotic and dead cells in a culture of rCHO cell line 2 when seeded at $0.5 \times 10\string^6$ vc/mL in 250 mL and 3 L shake flasks.
Figure 10:
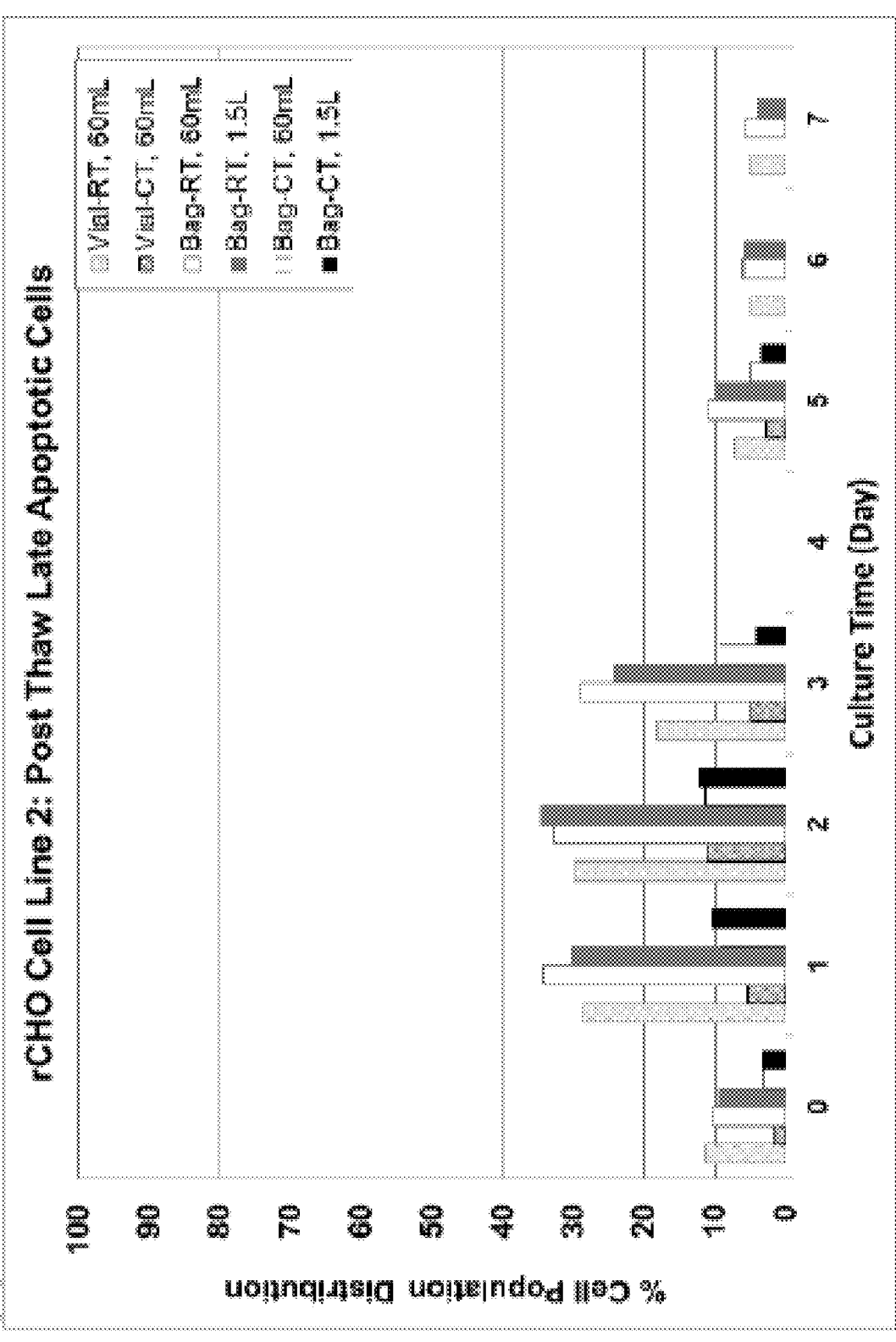
FIG. 10: is a graph depicting the percentage of late apoptotic and dead cells in a culture of rCHO cell line 2 when seeded at $1.0 \times 10\string^6$ vc/mL in 250 mL and 3 L shake flasks.
Figure 11:
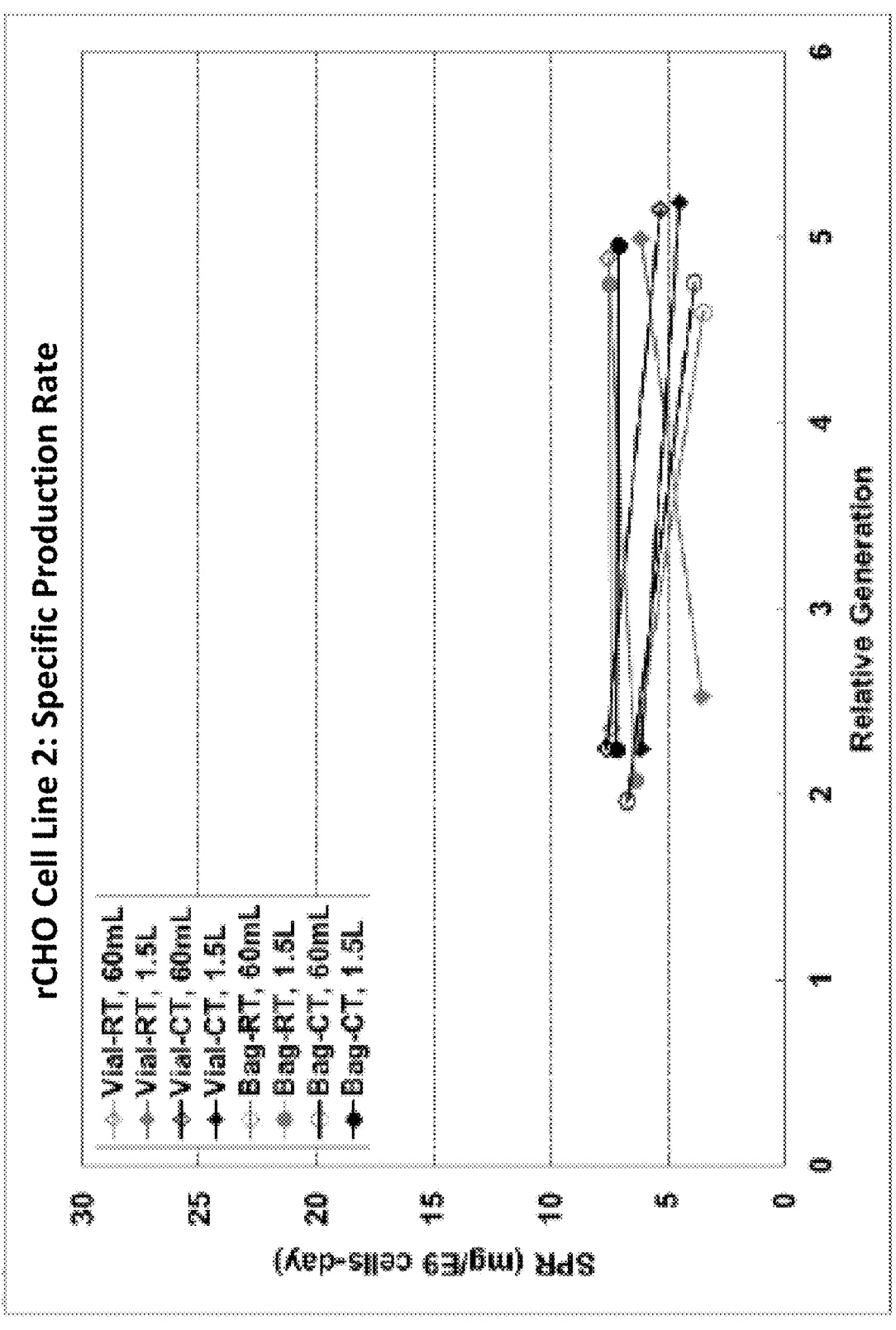
FIG. 11: is a graph depicting specific production rate (SPR) in shake flasks cultures of rCHO cell line 2 when seeded at $0.5 \times 10\string^6$ vc/mL in 250-mL and 3-L shake flasks.
Figure 12:
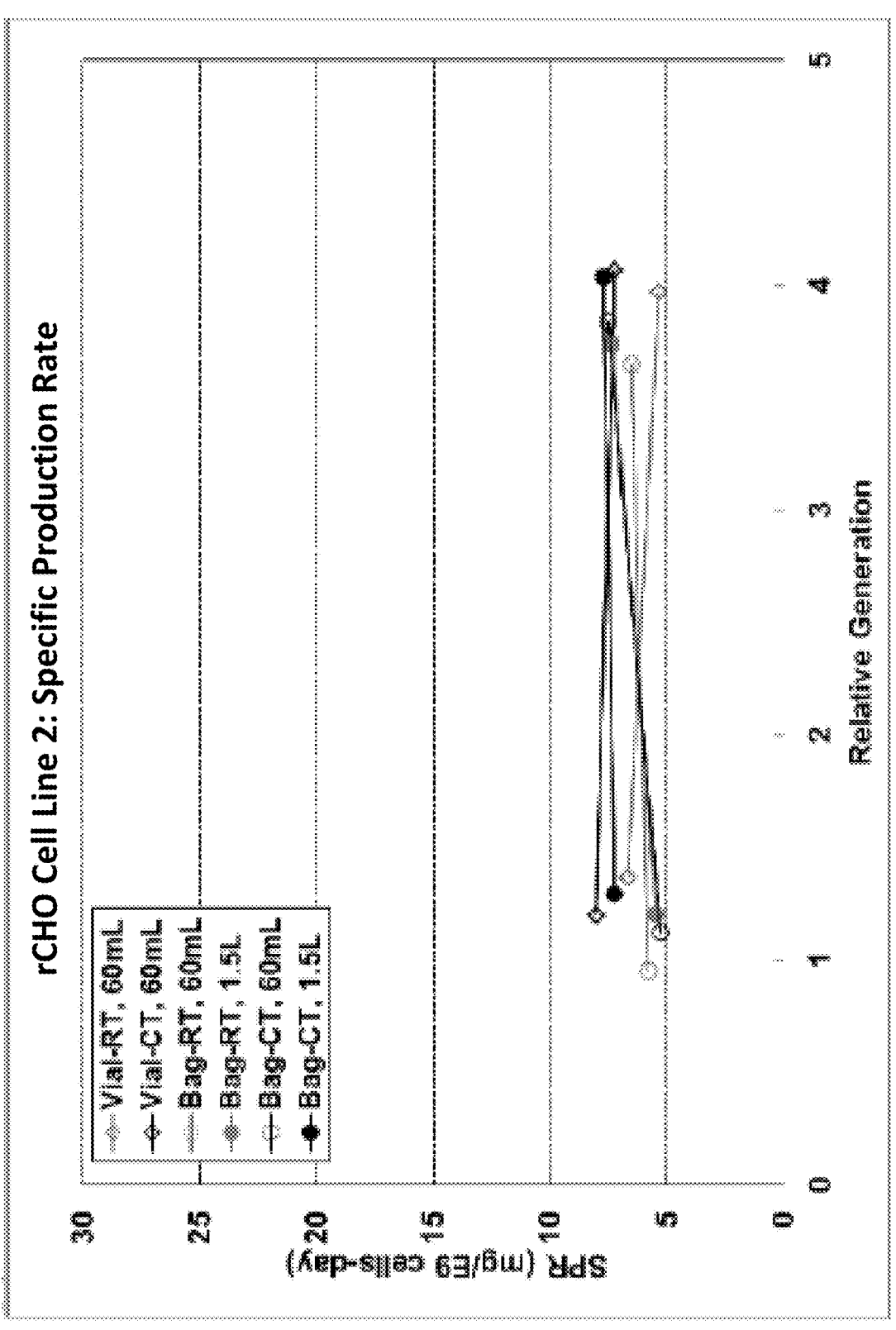
FIG. 12: is a graph depicting specific production rate (SPR) in shake flasks cultures of rCHO cell line 2 when seeded at $1.0 \times 10\string^6$ vc/mL in 250-mL and 3-L shake flasks.

FIGS. 7 and 8 are graphs demonstrating the cell growth (Xv; solid lines) and viability (dotted lines) profiles in 250-mL and 3-L shake flasks for UHD vials and bags created from the aforementioned cell culture conditions at room temperature and in well-controlled cold holding conditions (RT and CT, respectively). These UHD vials and bags recovered well with rapid post-freezing cell growth, high viability, low apoptosis, and comparable productivity when seeded at $0.5\times10^6$ vc/mL and $1.0\times10^6$ vc/mL in 250-mL and 3-L shake flasks. No difference was observed between UHD cryobags and cryovials at each holding conditions in terms of post thaw growth, viability, apoptosis, and productivity. However, vials and bags made at the well-controlled low temperature by a 4° C. jacketed spinner had faster growth, higher viability and lower apoptosis when compared to those made at room temperature. FIG. 9 and FIG. 10 show profiles of post thaw apoptosis of UHD banks when seeded at $0.5\times10^6$ vc/mL and $1.0\times10^6$ vc/mL respectively, and FIG. 11 and FIG. 12 depict the Specific Production Rate (SPR, RT—room temperature; CT—well controlled cold temperature)

Example 5: Ultra-High Density Cell Bank Performance in the 20-L WAVE Bioreactor Using rCHO 2

The parameters for the following experiment were as follows:

1) Cell bank: 100 mL UHD cryobag made at example 2

2) Bioreactor medium: CD CHO with 4 mM L-glutamine.

3) Post freezing Bioreactor: GE 20-L Cellbag; working volume: 10 L.

4) Bioreactor inoculum: post thaw culture from the thawed cryobag; seed density: about $5\times10^5$ vc/mL.

5) Bioreactor temperature: 37° C., $O_2$: 20%, $CO_2$: 5%, rock speed & angle: 22 rpm/8°

One 100 mL UHD cryobag was thawed. 50 mL of the thawed culture was inoculated into one 20-L WAVE bioreactor (A) directly with a total 10 L working volume. Another 50 mL was diluted slowly with cold medium first to reduce the potential cell damage induced by the large osmotic gradient, which was then inoculated into a second 20-L WAVE bioreactor (B) with a total 10 L working volume. Both bioreactors were operated at the same conditions.

Aliquots from both bioreactors were transferred to satellite shake flasks (60 mL working volume) for growth comparison. The bioreactor cultures were also compared to shake flask cultures (60 mL/250-mL shake flasks and 1.5 L/3-L shake flasks) with inoculum from another thawed 100 mL cryobag.

The two WAVE cultures performed very comparably in terms of post thaw cell growth, viability, and apoptosis. And cultures in both bioreactors were very comparable to not only those in the satellite shake flasks, but also those thawed and grown in shake flasks. These data suggest that one UHD cryobag could be directly thawed into 2×20-L WAVE bioreactors without the cold medium slow dilution with comparable performance to shake flasks, which will make the seed train process completely closed from bag thaw to WAVE bioreactor expansion.

Figure 13:
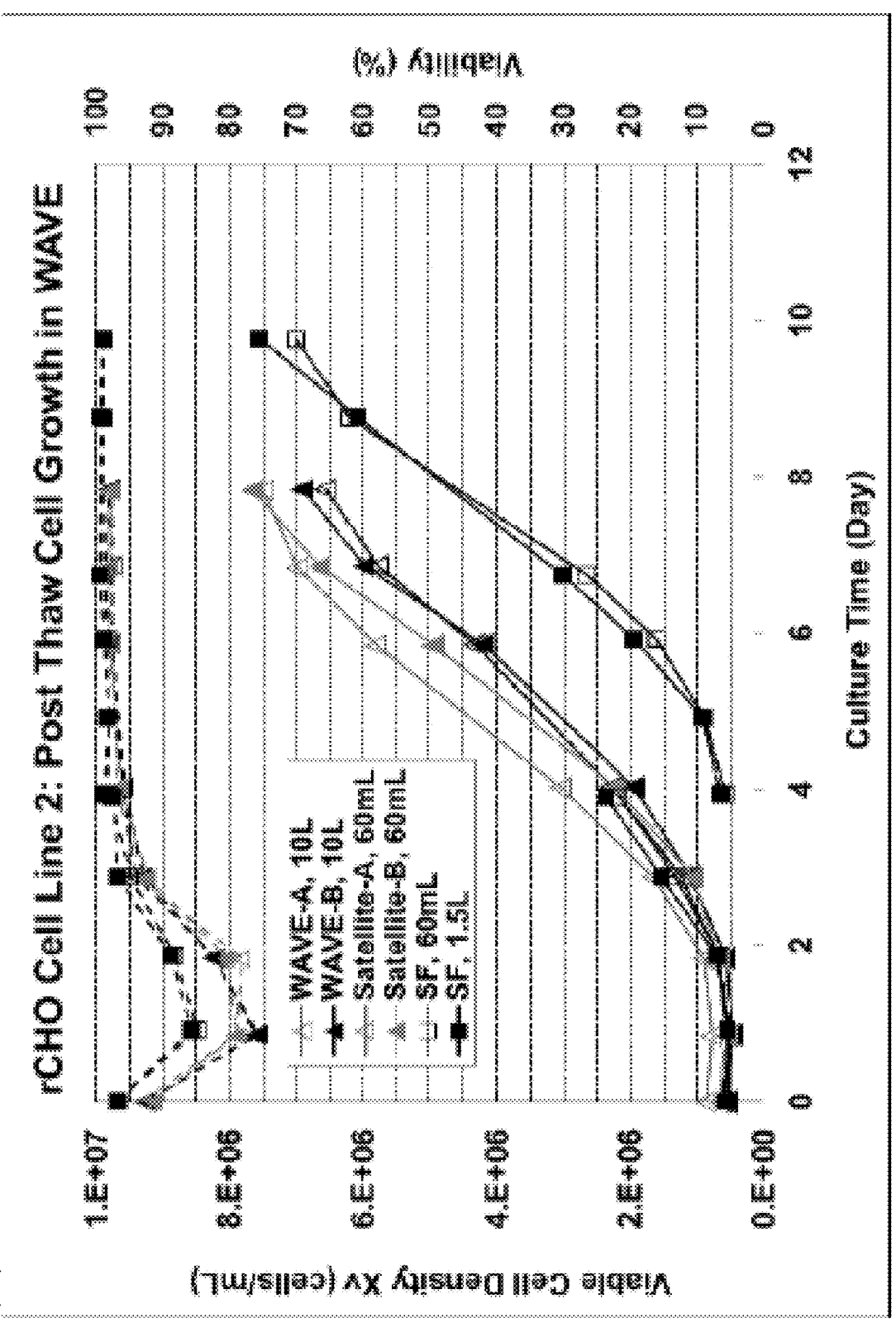
FIG. 13: is a graph depicting the cell growth in WAVE bags based on viable cell density Xv (cells/mL; solid lines) and viability (dotted lines) for rCHO cell line 2.
Figure 14:
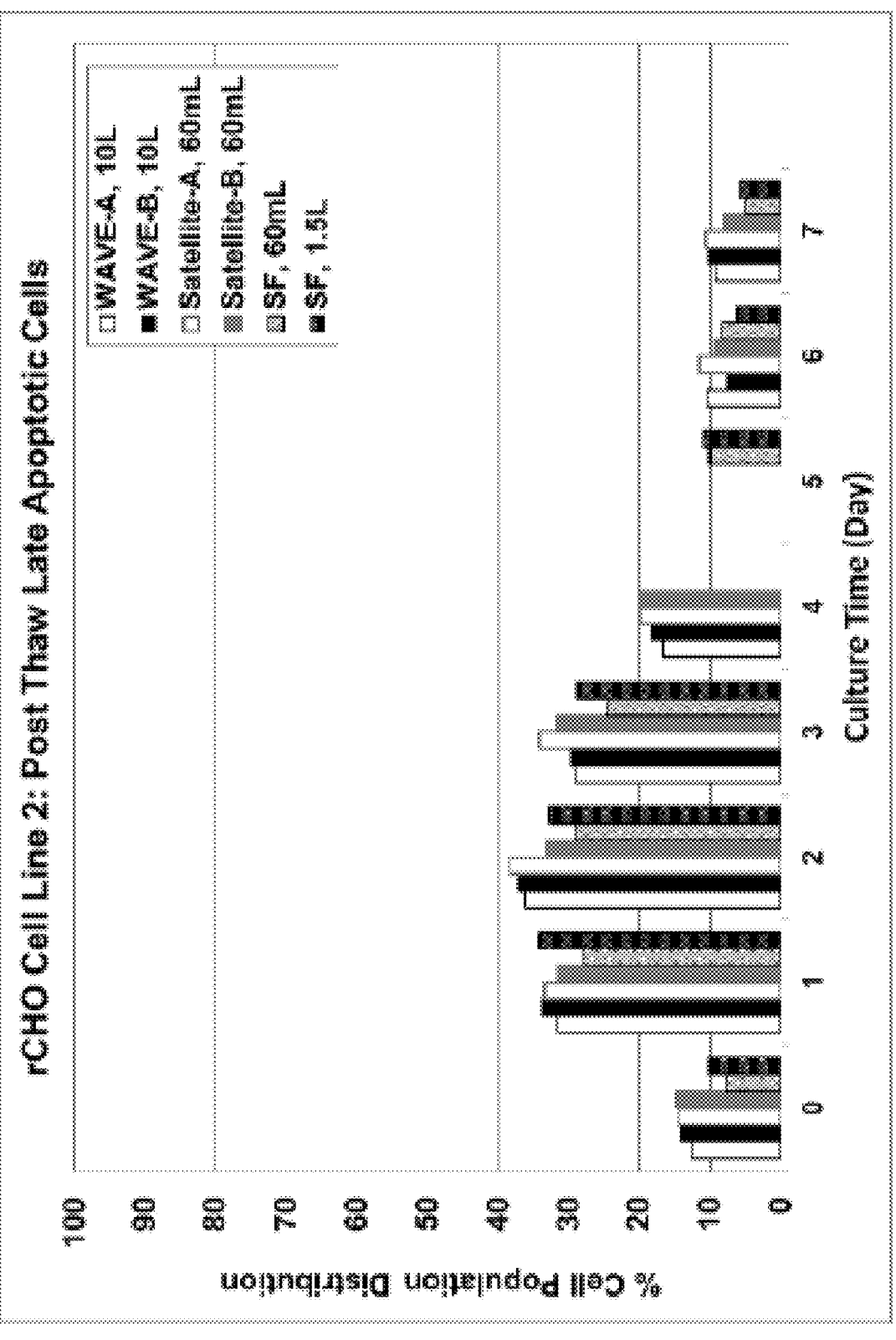
FIG. 14: is a graph depicting the percentage of late apoptotic and dead cells in a culture of rCHO cell line 2.

FIG. 13 is a graph demonstrating the cell growth (Xv; solid lines) and viability (dotted lines) profile in 20-L WAVE bags for UHD cryobag of rCHO cell line 2 created following the aforementioned cell culture conditions at room temperature shown in example 2.

Example 6: Ultra-High Density Cell Culture and Cell Bank Performance Using rCHO 3

The parameters for the following experiment were as follows:

1) $CO_2$ was decreased to 0% when Xv≥about $2\times10^7$ vc/mL (on day 8), base was then added afterwards when needed;

2) WAVE rock speed & angle: initially 22 rpm/10° (from day 0 to day 7); increased to 25 rpm/12° when POD $O_2$ increased from 21% to >30% (on day 7) to facilitate gas transfer (for supplying $O_2$ and removing $CO_2$);

3) Additional pure $O_2$ (100%) was supplied manually to the headspace when POD $O_2$>30% and Xv≥about $3\times10^7$ vc/mL (on day 9).

4) Total gas flow rate: 0.2 lpm initially (from day 0 to day 9), and increased to 0.4 lpm on day 9 when Xv≥about $3\times10^7$ vc/mL (POD $O_2$: pure $O_2$=3:1, total $O_2$: about 62%), and then to about 0.5 lpm on day 10 (POD $O_2$: pure $O_2$=1:1, total $O_2$: about 75%), to about 0.6 lpm on day 12 (POD $O_2$: pure $O_2$=1:2, total $O_2$: about 83%).

5) Cell specific perfusion rate: perfusion was started at 0.5 RV/day on day 2 and increased stepwise to maintain a low CSPR of ≥0.05 nL/cell-day 6) Seed train and Bioreactor medium: CD CHO with 4 mM L-glutamine 7) Bioreactor: GE custom 10-L Cellbag perfusion bioreactor with one dip tube; working volume: 5 L;

8) Bioreactor inoculum: shake flask seed train; seed density: about $5\times10^5$ vc/mL 9) Cell retention methods: ATF4 (0.2 μm pore size)

10) Temperature of cell culture: 37° C.

11) Freeze down: CryoMed™ controlled-rate freezer

12) Post banking evaluation: shake flask (two passages) and 20-L WAVE (one passage), Xv, viability, apoptosis, productivity were evaluated.

13) Post banking evaluation medium: CD CHO with 4 mM L-glutamine

Figure 15:
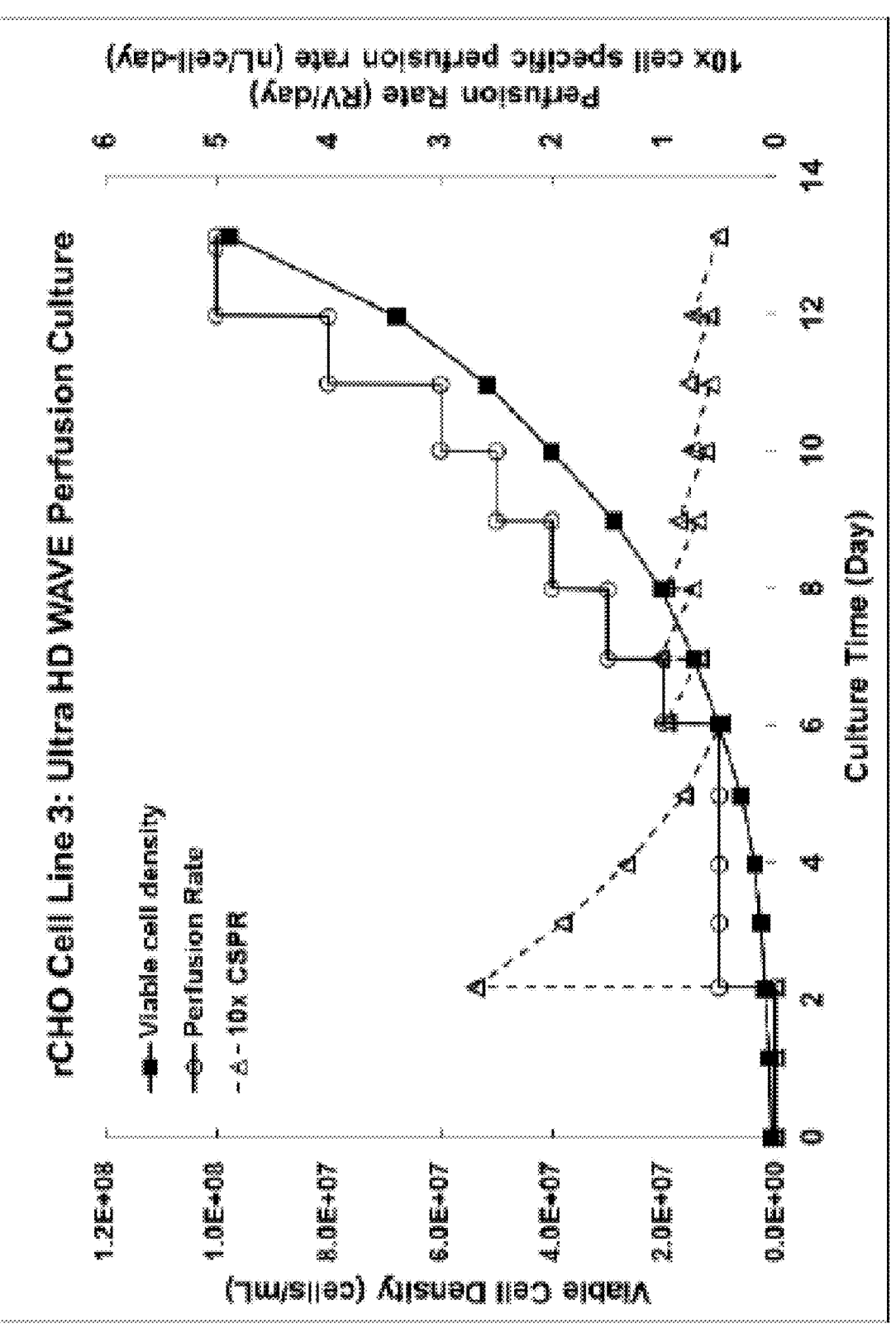
FIG. 15: is a graph depicting the viable cell density (cells/mL), perfusion rate (RV/day) and 10× cell specific perfusion rate (nL/cell-day) in an exemplary culture of rCHO cell line 3.
Figure 16:
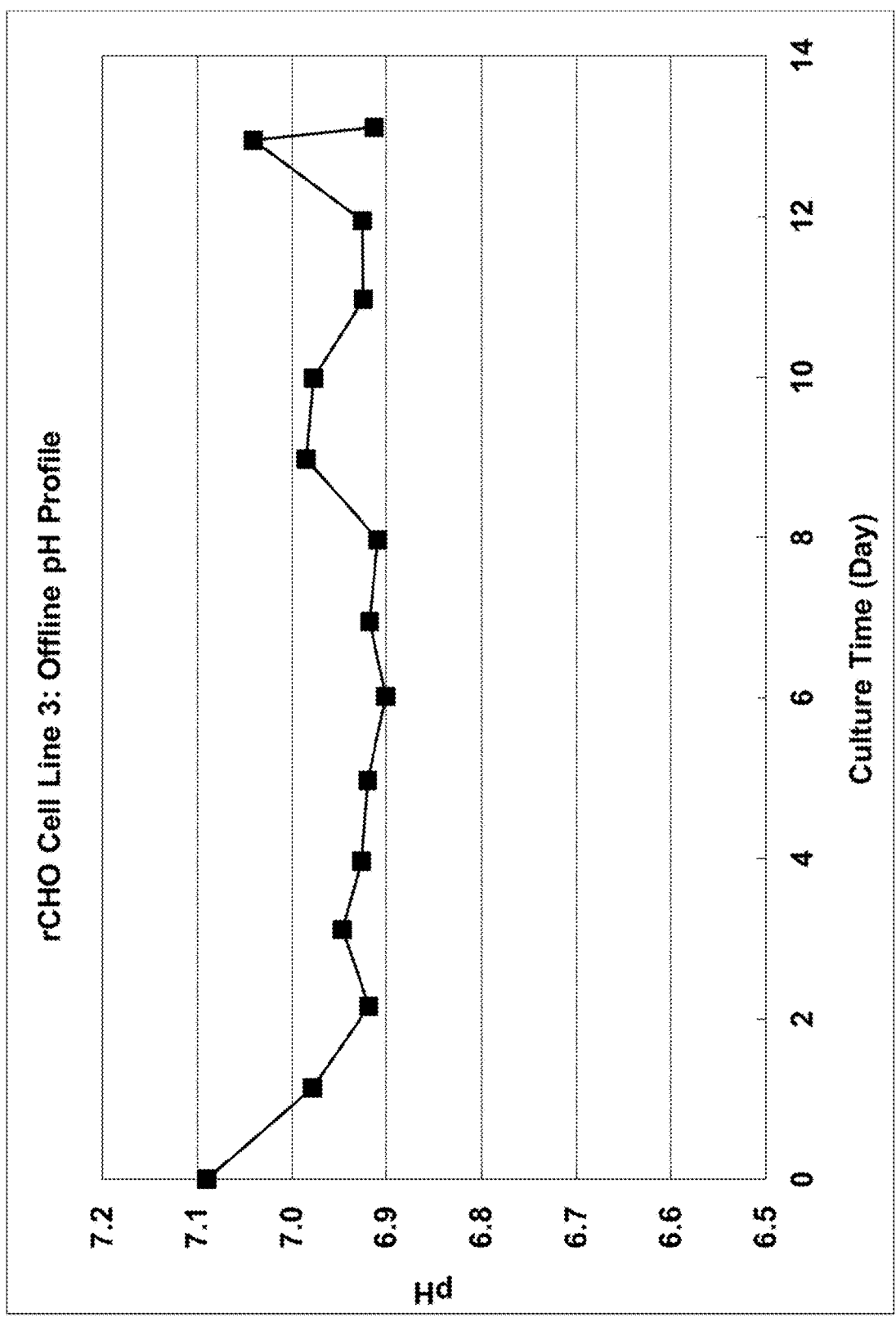
FIG. 16: is a graph depicting the offline pH profile in a culture of rCHO cell line 3.

Ultra HD cell culture and cell bank performance (post-freezing and thaw) were tested for rCHO cell line 3. The viable cell density (cells/mL), perfusion rate in reactor volumes/day, and 10×CSPR (10× cell specific perfusion rate in nL/cell-day) for the ultra-high density perfusion culture are shown in FIG. 15. FIG. 16 shows the offline pH profile of the culture. UHD (ultra-high density) 5-mL vials and 100-mL UHD bags were made using the ultra-high density perfusion culture at two different DMSO holding conditions: 1) room temperature (RT, approximately 22-25° C.); and 2) a controlled cold temperature (CT, approximately 5° C. using a 4° C. jacketed spinner).

Figure 17A:
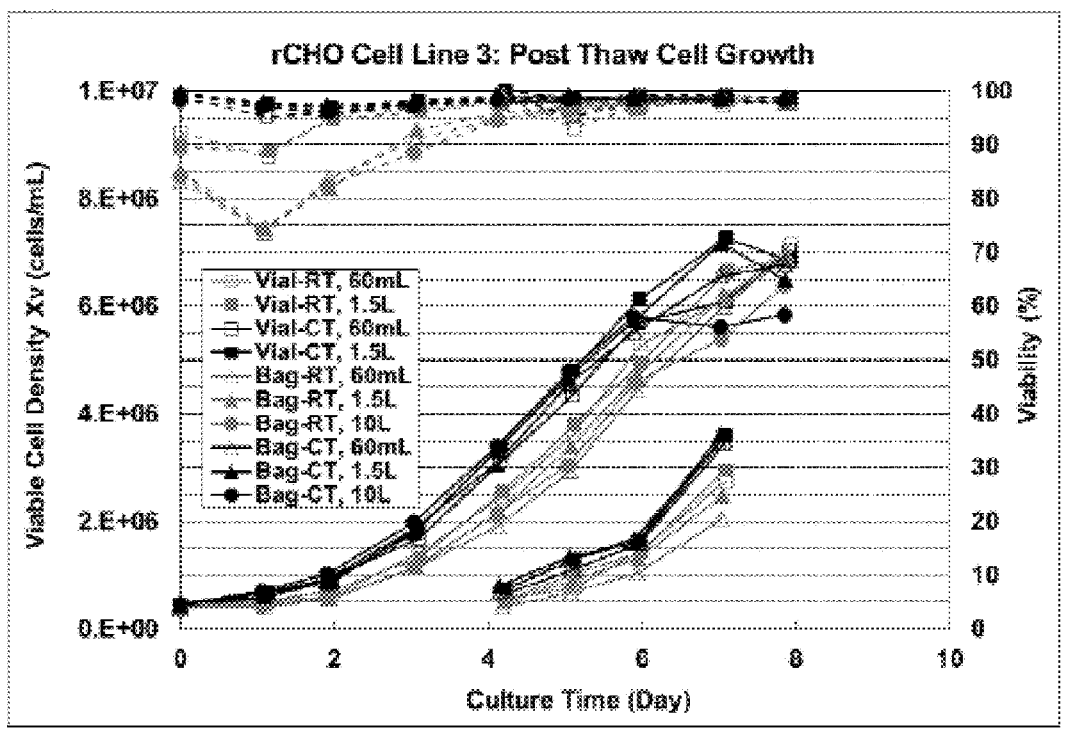
FIGS. 17A-17C: are a series of graphs depicting (FIG. 17A) the cell growth (solid lines) and viability (dotted lines), (FIG. 17B) the percentage of late apoptotic and dead cells, and (FIG. 17C) the specific production rate (SPR) in shake flasks cultures of rCHO cell line 3.
Figure 17B:
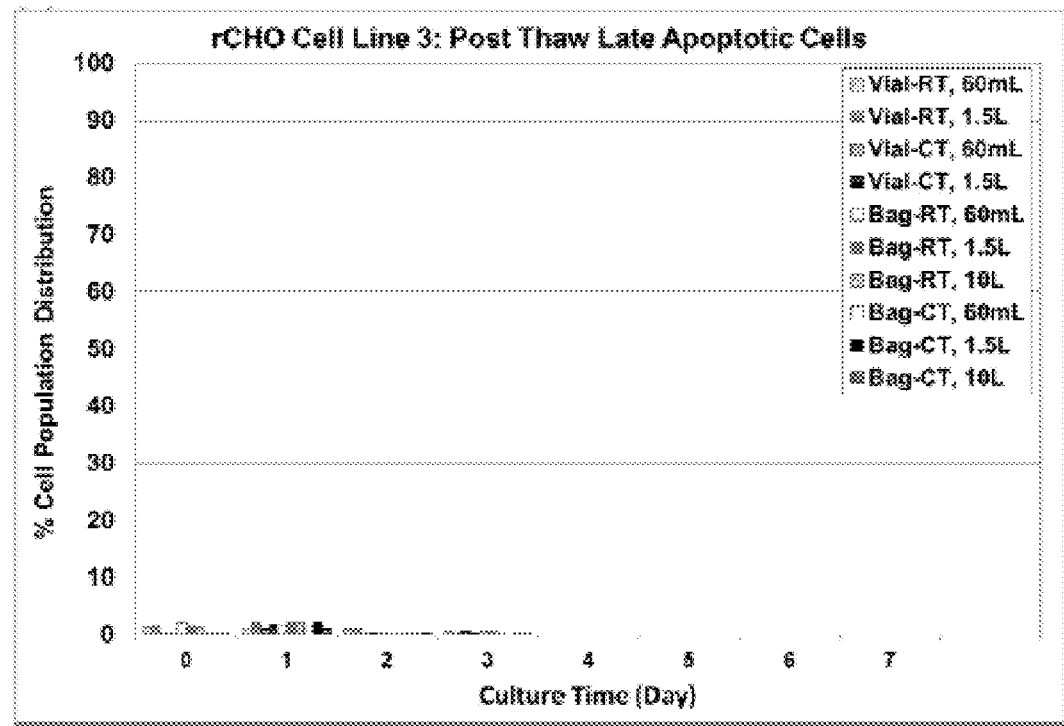
Figure 17C:
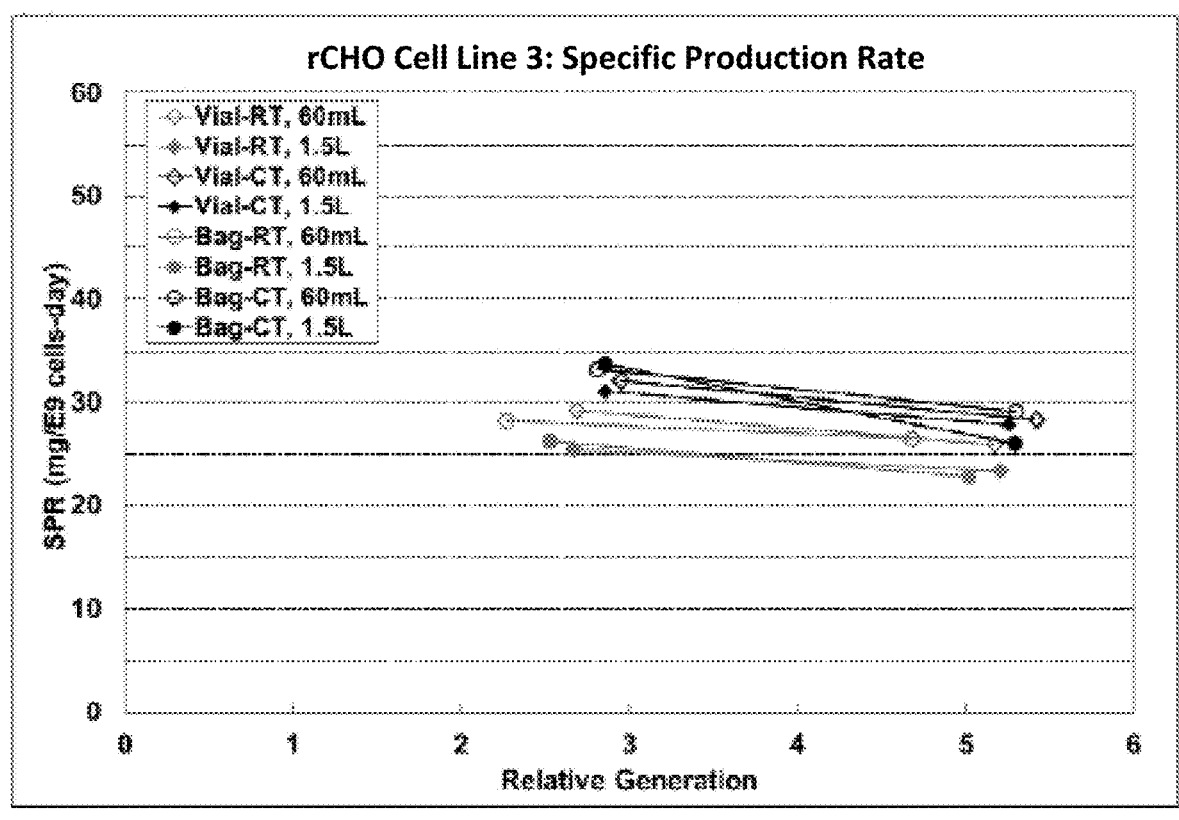

All post thaw cultures from UHD vials and UHD bags recovered well with rapid growth, low apoptosis, and comparable productivity. UHD bags and vials made at the well-controlled cold holding condition were comparable, with a slightly faster growth and higher viability (>95%) at the first passage than those made at room temperature. The UHD bag had comparable post-thaw performance in shake flasks and WAVE bioreactors. It then also suggests that one UHD cryobag could be directly thawed into 2×20-L WAVE bioreactors, which will make the seed train process completely closed from bag thaw to WAVE bioreactor expansion. FIG. 17A is a graph demonstrating the cell growth (Xv; solid lines) and viability (dotted lines) profiles in 250-mL and 3-L shake flasks and 20-L WAVEs for UHD vials and bags created from the aforementioned cell culture conditions at room temperature and in well-controlled cold holding conditions (RT and CT, respectively). FIGS. 17B-17C show profiles of post thaw apoptosis and specific production rate (SPR).

Figure 18:
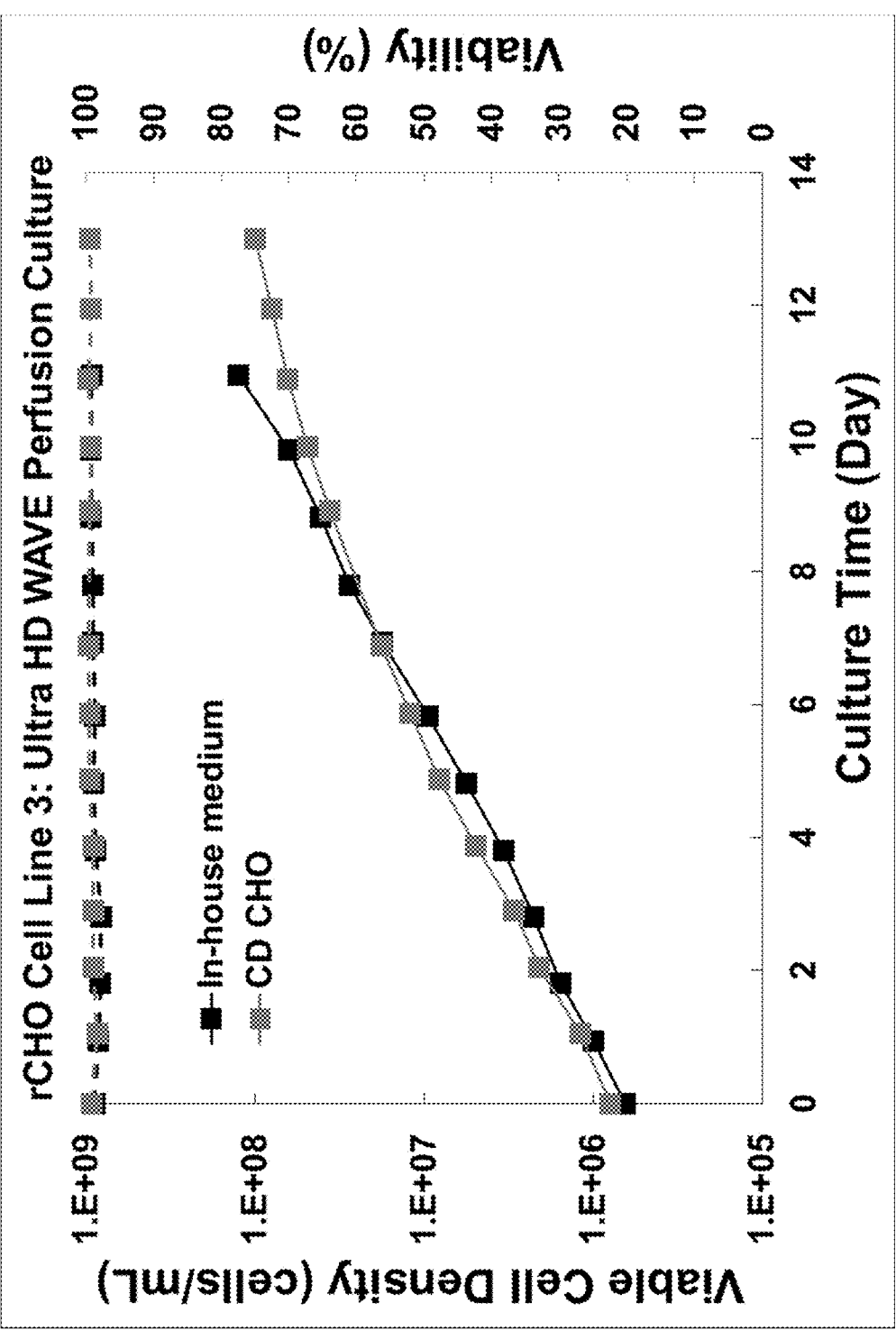
FIG. 18: is a graph comparing the viable cell density (cells/mL, solid lines) and viability (dotted lines) with in-house medium (black) and CD CHO medium (gray) in an exemplary culture of rCHO cell line 3.
Figure 19:
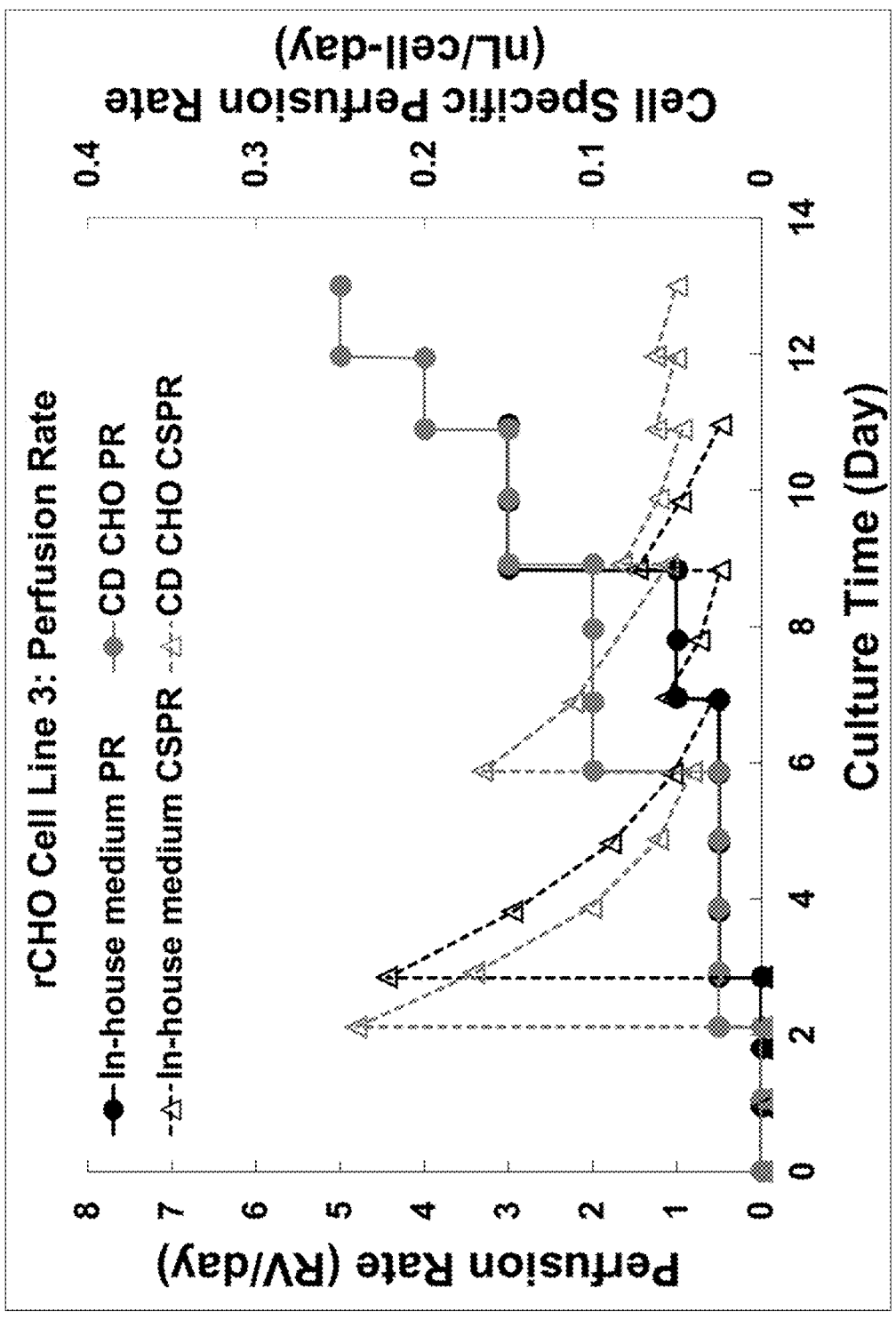
FIG. 19: is a graph comparing the perfusion rate (circles, solid lines) and cell specific perfusion rate (triangles, dotted lines) with in-house medium (black) and CD CHO medium (gray) in an exemplary culture of rCHO cell line 3.

Example 7: Reduction of Media Usage in the Ultra-High Density Perfusion Culture Process Using rCHO 3 rCHO cell line 3 was grown at a low cell specific perfusion rate (CSPR) of ≥0.025 nL/cell-day using an in-house developed medium. A 10-L custom WAVE Cellbag coupled with ATF4 was used for the perfusion culture. The culture reached viable cell density of about 1.25×10⁸ vc/mL on day 11 with perfusion rate up to 3 reactor volumes/day. The culture viability was >97% throughout the bioreactor culture process. Media usage was reduced to about 50% when compared to the same culture conditions using the commercial medium. However, cell growth was observed to be slightly more rapid than when using the commercial CD CHO medium. The culture was harvested directly (and without concentration) to generate UHD banks in 5-mL vials and 100-mL cryobags at the well-controlled cold DMSO holding temperature by using a 4° C. jacketed spinner. Post-banking studies demonstrated that both the vial and cryobag UHD banks recovered well after thawing in shake flasks, with fast growth, high viability (>95%), and comparable productivity. Additionally, one cryobag was thawed into two 20-L WAVE bioreactors and demonstrated comparable cell growth and viability to the shake flasks. FIG. 18 is a graph comparing the viable cell density (cells/mL, solid lines) and viability (dotted lines) with in-house medium (black) and CD CHO medium (gray) in an exemplary culture of rCHO cell line 3. FIG. 19 is a graph comparing the perfusion rate (circles, solid lines) and cell specific perfusion rate (triangles, dotted lines) with in-house medium (black) and CD CHO medium (gray) in an exemplary culture of rCHO cell line 3.

Figure 20:
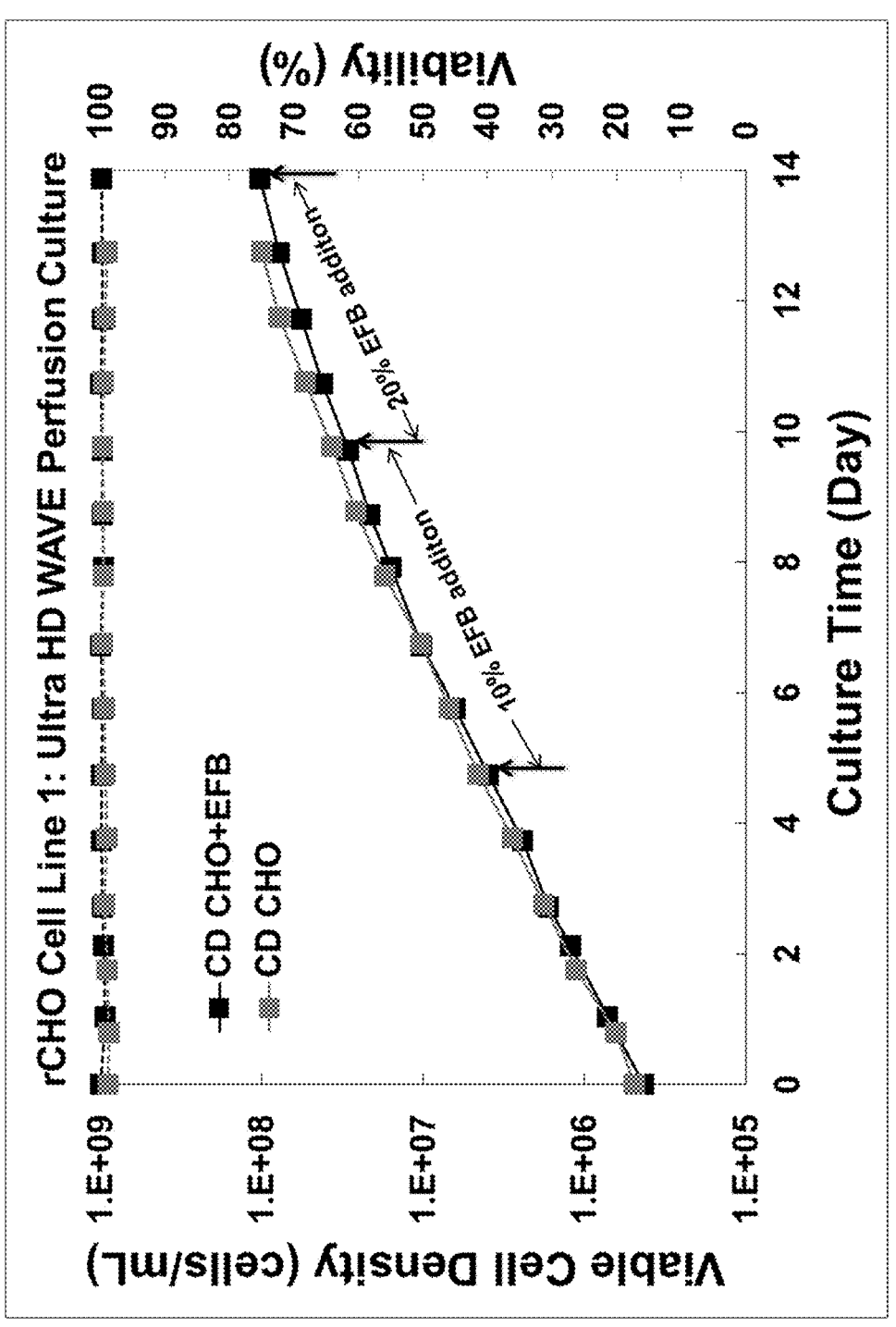
FIG. 20: is a graph comparing the viable cell density (cells/mL, solid lines) and viability (dotted lines) with CD CHO medium supplemented with Efficient Feed B (black) and CD CHO medium (gray) in an exemplary culture of rCHO cell line 1.
Figure 21:
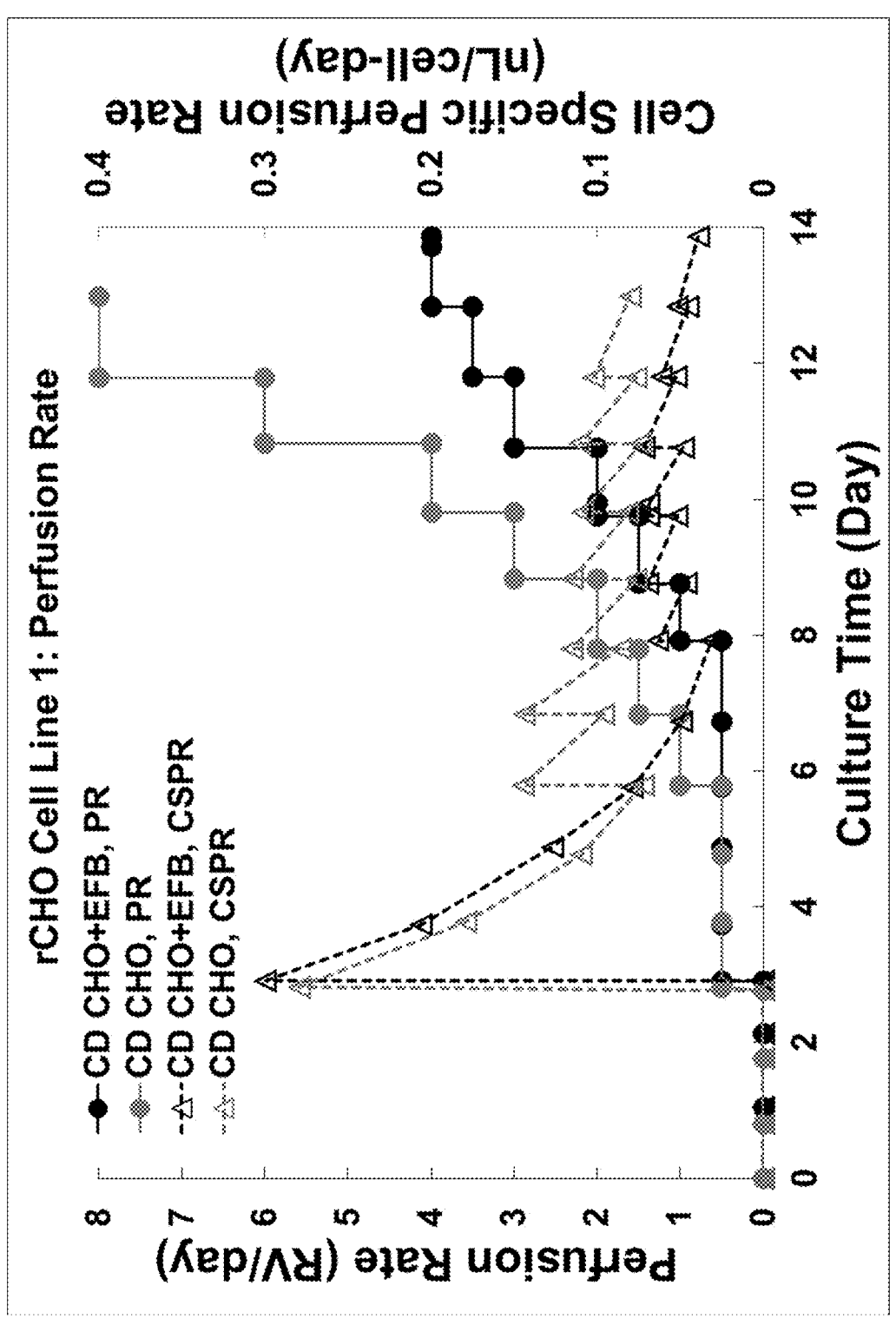
FIG. 21: is a graph comparing the perfusion rate (circles, solid lines) and cell specific perfusion rate (triangles, dotted lines) with CD CHO medium supplemented with Efficient Feed B (black) and CD CHO medium (gray) in an exemplary culture of rCHO cell line 1.

Example 8: Reduction of Media Usage in the Ultra-High Density Perfusion Culture Process Using rCHO 1 rCHO cell line 1 was grown using commercial CD CHO medium supplemented with Efficient Feed B (EFB) and maintained at a low cell specific perfusion rate (CSPR) at ≥0.04 nL/cell-day. The GE 10-L WAVE perfusion Cellbag with a built-in filter was used as the perfusion culture bioreactor. For comparison, the commercial CD CHO medium without any nutrient supplement was also tested. The culture without EFB addition reached viable cell density of about 1.0×10⁸ vc/mL on day 13 with perfusion rate up to 8 reactor volumes/day. By adding 10% EFB into CD CHO medium from day 5 to day 10 and 20% EFB from day 10 to day 14, the culture reached viable cell density of about 1.03×10⁸ vc/mL on day 14 with a perfusion rate up to 4 reactor volumes/day. Therefore, with the EFB addition, comparable UHD perfusion cell culture was achieved with an approximate 50% reduction in medium usage. FIG. 20 is a graph comparing the viable cell density (cells/mL, solid lines) and viability (dotted lines) with CD CHO medium supplemented with Efficient Feed B (black) and CD CHO medium (gray) in an exemplary culture of rCHO cell line 1. FIG. 21 is a graph comparing the perfusion rate (circles, solid lines) and cell specific perfusion rate (triangles, dotted lines) with CD CHO medium supplemented with Efficient Feed B (black) and CD CHO medium (gray) in an exemplary culture of rCHO cell line 1.

Example 9: Scaling Up the Ultra-High Density Perfusion Process Using rCHO 3

Figure 22:
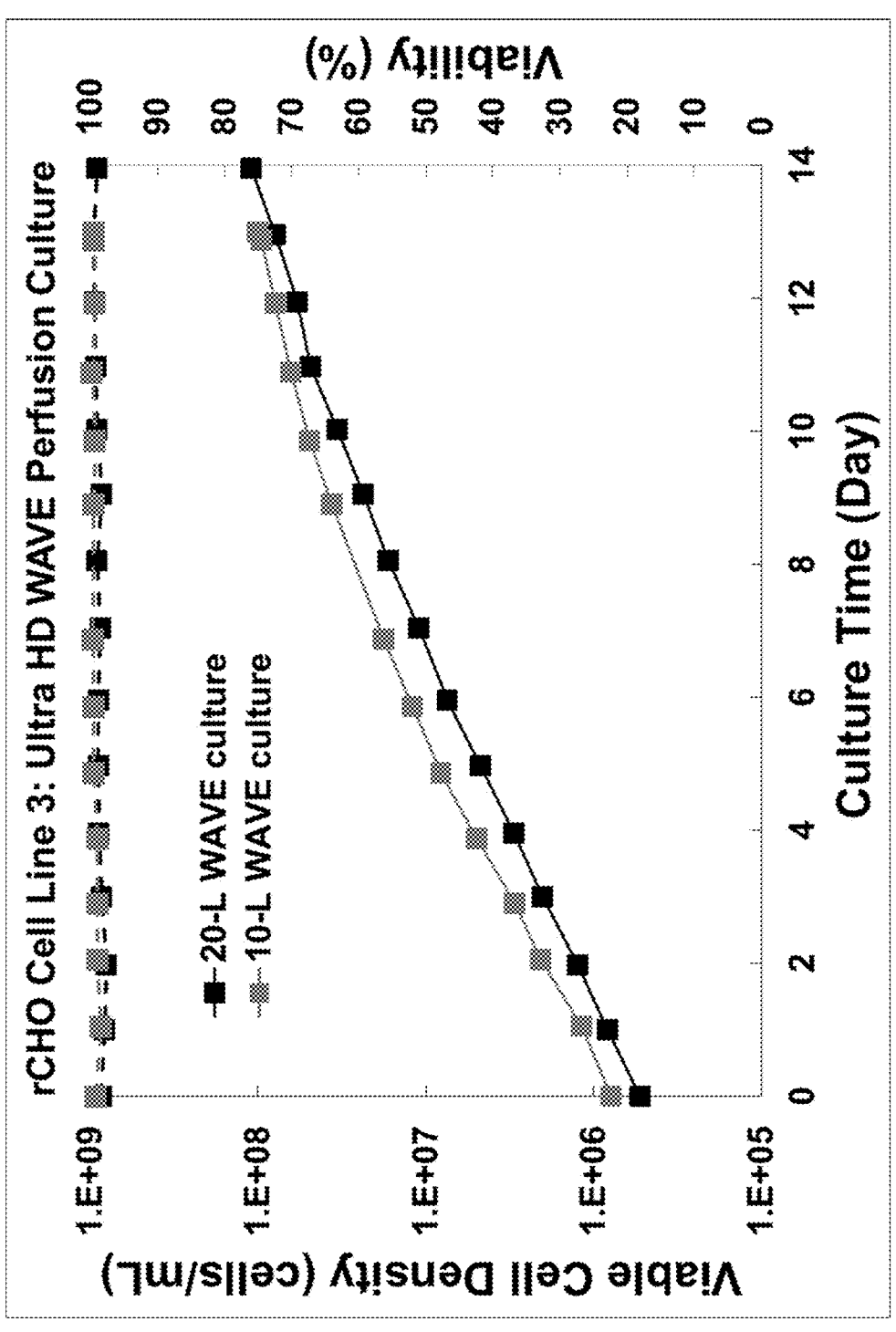
FIG. 22: is a graph depicting the viable cell density (cells/mL, solid lines) and viability (dotted lines) using the 20-L WAVE bioreactor (10-L working volumes, black) and 10-L WAVE bioreactor (5-L working volume, grey) in an exemplary culture of rCHO cell line 3.

A 20-L WAVE Cellbag was customized to couple with ATF4 for supporting 10 L UHD perfusion culture. rCHO cell line 3 growth in commercial CD CHO medium was tested. The culture reached viable cell density of about 1.1×10⁸ vc/mL on day 14 with a perfusion rate up to 5 reactor volumes/day. The cell specific perfusion rate (CSPR) was maintained at ≥0.04 nL/cell-day and viability was >97%. The cell growth was comparable to that using a 10-L WAVE Cellbag with 5 L working volume. FIG. 22 depicts the viable cell density (cells/mL, solid lines) and viability (dotted lines) using the 20-L WAVE bioreactor (10-L working volumes, black) and 10-L WAVE bioreactor (5-L working volume, grey) in an exemplary culture of rCHO cell line 3. The culture was able to be harvested directly for making about 90×100 mL cryobags.

Example 10: Evaluation of Ultra-High Density Cryobag Banks after One Year Storage in Vapor Phase Liquid Nitrogen Storage Freezers Using rCHO 2 and rCHO 3

100 mL UHD cryobags (about 1.0×10⁸ vc/mL, 100 mL per cryobag) from rCHO cell line 2 and 3 were tested for post-thaw performance and compared to the 0 time point (when the banks were frozen down and transferred to vapor phase liquid N₂ storage overnight). Comparable post-thaw cell growth, viability, and productivity were observed for cells at time point 0 and at one year.

We claim:

1. A method for producing an ultra-high density frozen mammalian cell bank directly from a population of cultured cells, the method comprising:

a) culturing the mammalian cells in a perfusion bioreactor to obtain the ultra-high density cell population with a concentration of at least about 1.0×10⁸ cells/mL, wherein said perfusion bioreactor is coupled to a cell retention system;

b) harvesting the ultra-high density population directly without performing a concentration step after culturing the mammalian cells in the perfusion bioreactor that is coupled to the cell retention system; and c) cryopreserving the harvested ultra-high density cell population by adding a cryoprotectant to produce an ultra-high density frozen cell bank, wherein the ultra-high density frozen cell bank has a concentration of at least about $1.0 \times 10^8$ cells/mL and at least 95% post-thaw viability.

2. The method of claim 1, wherein the ultra-high density cell population has a concentration selected from the group consisting of about $1.1 \times 10^8$ cells/mL, about $1.2 \times 10^8$ cells/mL, about $1.3 \times 10^8$ cells/mL, about $1.4 \times 10^8$ cells/mL, about $1.5 \times 10^8$ cells/mL, about $1.6 \times 10^8$ cells/mL, about $1.7 \times 10^8$ cells/mL, about $1.8 \times 10^8$ cells/mL, about $1.9 \times 10^8$ cells/mL, and about $2.0 \times 10^8$ cells/mL.

3. The method of claim 1, wherein the cryopreserving comprises adding dimethyl sulphoxide (DMSO) to the ultra-high density cell population at a final concentration of about 5% to about 10%, vol/vol.

4. The method of claim 1, wherein the ultra-high density frozen cell bank is contained in a vial or a cryobag and comprises about $4.5 \times 10^8$ cells/vial or about $100 \times 10^8$ cells/cryobag.

5. The method of claim 1, wherein the perfusion rate in the perfusion bioreactor is between about 0.02 nL/cell/day to about 0.5 nL/cell/day.

6. The method of claim 1, wherein the perfusion rate in the perfusion bioreactor is between 0 and 15 reactor volumes per day.

7. The method claim 1, wherein the perfusion bioreactor cell culture has a dissolved oxygen concentration (DO) of at least about 30%.

8. The method of claim 1, wherein the mammalian cells are selected from the group consisting of: CHO, CHO-DBX11, CHO-DG44, CHO-S, CHO-K1, Vero, BHK, HeLa, COS, MDCK, HEK-293, NIH-3T3, W138, BT483, Hs578T, HTB2, BT20, T47D, NS0, CRL7030, HsS78Bst cells, PER.C6, SP2/0-Agl4, and hybridoma cells.

9. The method of claim 1, wherein the mammalian cells are transfected cells or the cells express a therapeutic protein.

10. The method of claim 1, wherein the bioreactor is rocked at 25 rpm with a rock angle of 12° or at 22 rpm with a rock angle of 10°.

11. The method of claim 1, wherein the ultra-high density cell population is cryopreserved by any one of the following:

(i) cooled to and maintained at a temperature of about 4° C. prior to and during the addition of the cryoprotectant and dispensing; or (ii) maintained at a temperature of about 20° C. to about 26° C. prior to and during the addition of the cryoprotectant; or (iii) maintained at an uncontrolled cold temperature by using an ice water bath prior to and during the addition of the cryoprotectant.

12. The method of claim 1, wherein a total gas flow rate is initially set to 0.2 liters per minute (lpm), followed by increasing the total gas flow rate to 0.4 lpm when the cell concentration is about $3 \times 10^7$ cells/mL to about $4 \times 10^7$ cells/mL.

13. The method of claim 1, wherein the $CO_2$ concentration is reduced to 0% when the cell concentration is about $2 \times 10^7$ cells/mL to about $5 \times 10^7$ cells/mL.

14. A method for producing a culture of mammalian cells from an ultra-high density frozen cell bank, the method comprising thawing and culturing the ultra-high density frozen cell bank with a concentration of at least about $1.0 \times 10^8$ cells/mL in a perfusion bioreactor to obtain the culture of mammalian cells, wherein the ultra-high density frozen cell bank was produced by harvesting a cell culture directly from a bioreactor, wherein said bioreactor is coupled to a cell retention system, without performing any concentration steps after culturing the mammalian cells in the perfusion bioreactor and cryopreserving the harvested cell culture after adding a cryoprotectant, and wherein the cultured mammalian cells have at least 95% post-thaw viability.

15. The method of claim 14, wherein the ultra-high density frozen cell bank has a concentration selected from the group consisting of about $1.1 \times 10^8$ cells/mL, about $1.2 \times 10^8$ cells/mL, about $1.3 \times 10^8$ cells/mL, about $1.4 \times 10^8$ cells/mL, about $1.5 \times 10^8$ cells/mL, about $1.6 \times 10^8$ cells/mL, about $1.7 \times 10^8$ cells/mL, about $1.8 \times 10^8$ cells/mL, about $1.9 \times 10^8$ cells/mL, and about $2.0 \times 10^8$ cells/mL.

16. The method of claim 14, wherein the mammalian cells are selected from the group consisting of: CHO, CHO-DBX11, CHO-DG44, CHO-S, CHO-K1, Vero, BHK, HeLa, COS, MDCK, HEK-293, NIH-3T3, W138, BT483, Hs578T, HTB2, BT20, T47D, NS0, CRL7030, HsS78Bst cells, PER.C6, SP2/0-Agl4, and hybridoma cells.

17. The method of claim 14, wherein the cells are transfected cells or the cells express a therapeutic protein.

18. The method of claim 14, wherein the cryoprotectant comprises dimethyl sulphoxide (DMSO) at a final concentration of about 5% to about 10%, vol/vol of the cell culture.

19. The method of claim 14, wherein the ultra-high density frozen cell bank is contained in a vial or a cryobag and comprises about $4.5 \times 10^8$ cells/vial or about $100 \times 10^8$ cells/cryobag.

20. The method of claim 14, wherein the cell culture is cryopreserved by any one of the following:

(i) cooled to and maintained at a temperature of about 4° C. prior to and during the addition of the cryoprotectant and dispensing; or (ii) maintained at a temperature of about 20° C. to about 26° C. prior to and during the addition of the cryoprotectant; or (iii) maintained at an uncontrolled cold temperature by using an ice water bath prior to and during the addition of the cryoprotectant.

21. A method for producing an ultra-high density frozen cell bank, the method comprising:

a) harvesting a culture of mammalian cells directly from a bioreactor, wherein the bioreactor is coupled to a non-centrifugal cell retention device, and wherein the harvesting is conducted without performing any concentration step after culturing the mammalian cells in the bioreactor that is coupled to the non-centrifugal cell retention device; and b) cryopreserving the harvested culture by adding a cryoprotectant to produce the ultra-high density frozen cell bank, wherein the ultra-high density frozen cell bank has a concentration of at least about $1.0 \times 10^8$ cells/mL and at least 95% post-thaw viability in a perfusion culture.

* * * * *